US011406371B2

(12) United States Patent
Williams et al.

(10) Patent No.: US 11,406,371 B2
(45) Date of Patent: Aug. 9, 2022

(54) MODULAR RETRACTOR SYSTEM AND METHOD OF USE

(71) Applicant: Institute for Musculoskeletal Science and Education, Ltd., King of Prussia, PA (US)

(72) Inventors: John Williams, Fort Wayne, IN (US); Seth Anderson, Mount Gretna, PA (US); Megan Stauffer, Wayne, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 0 days.

(21) Appl. No.: 17/155,848

(22) Filed: Jan. 22, 2021

(65) Prior Publication Data

US 2021/0361274 A1    Nov. 25, 2021

Related U.S. Application Data

(60) Provisional application No. 62/939,143, filed on Nov. 22, 2019.

(51) Int. Cl.
*A61B 17/02* (2006.01)
*A61F 2/46* (2006.01)
*A61B 90/35* (2016.01)
*A61B 17/00* (2006.01)
*A61B 17/56* (2006.01)

(52) U.S. Cl.
CPC ........ *A61B 17/025* (2013.01); *A61B 17/0206* (2013.01); *A61B 90/35* (2016.02); *A61F 2/4611* (2013.01); *A61B 2017/00473* (2013.01); *A61B 2017/0256* (2013.01); *A61B 2017/564* (2013.01); *A61B 2560/0443* (2013.01)

(58) Field of Classification Search
CPC ..... A61B 17/02; A61B 17/0206; A61B 17/32; A61F 2/4611
See application file for complete search history.

(56) References Cited

U.S. PATENT DOCUMENTS

| 5,303,694 A | 4/1994 | Mikhail |
| 5,902,233 A * | 5/1999 | Farley ................ A61B 17/0206 600/213 |
| 5,928,139 A * | 7/1999 | Koros ................ A61B 17/0206 600/205 |

(Continued)

FOREIGN PATENT DOCUMENTS

CN    202654170 U    1/2013

OTHER PUBLICATIONS

International Search Report and Written Opinion dated Aug. 13, 2021 in PCT Application No. PCT/US2021/14677.

(Continued)

*Primary Examiner* — Eduardo C Robert
*Assistant Examiner* — Steven J Cotroneo
(74) *Attorney, Agent, or Firm* — Plumsea Law Group, LLC

(57) ABSTRACT

A retractor system for use in preparing an area of the body for a surgical procedure is disclosed. The retractor system includes retractor blades that can be independently inserted and positioned within the body. The system also includes articulating arms that can be used to secure the retractor blades to one another and to rigidly fix the retractor blades in place relative to an operating table or other fixed structure.

19 Claims, 22 Drawing Sheets

(56) References Cited

U.S. PATENT DOCUMENTS

| | | | |
|---|---|---|---|
| 5,931,777 A * | 8/1999 | Sava | A61B 17/02 600/213 |
| 5,944,658 A | 8/1999 | Koros et al. | |
| 5,984,865 A | 11/1999 | Farley et al. | |
| 7,556,600 B2 | 7/2009 | Landry et al. | |
| 7,785,253 B1 * | 8/2010 | Arambula | A61B 1/32 600/219 |
| 7,850,608 B2 | 12/2010 | Hamada | |
| 7,931,589 B2 | 4/2011 | Cohen et al. | |
| 7,946,982 B2 | 5/2011 | Hamada | |
| 7,981,029 B2 | 7/2011 | Branch et al. | |
| 8,114,016 B2 * | 2/2012 | Lo | A61B 17/0206 600/202 |
| 8,303,499 B2 | 11/2012 | Hamada | |
| 8,353,826 B2 | 1/2013 | Weiman | |
| 8,636,657 B2 | 1/2014 | Hamada | |
| 8,876,904 B2 | 11/2014 | Pimenta et al. | |
| 8,968,363 B2 | 3/2015 | Weiman et al. | |
| 9,095,301 B2 | 8/2015 | Hamada | |
| 9,451,940 B2 | 9/2016 | Spann | |
| 9,486,199 B2 | 11/2016 | Pimenta et al. | |
| 9,622,732 B2 | 4/2017 | Martinelli et al. | |
| 9,848,862 B2 | 12/2017 | Bass et al. | |
| 10,085,854 B2 | 10/2018 | Spann | |
| 10,130,348 B2 | 11/2018 | Cryder et al. | |
| 10,238,375 B2 * | 3/2019 | O'Connell | A61B 17/0293 |
| 10,278,786 B2 * | 5/2019 | Friedrich | A61B 17/0206 |
| 10,687,830 B2 | 6/2020 | Garcia-Bengochea et al. | |
| 10,959,860 B2 | 3/2021 | Spann | |
| 2001/0037123 A1 * | 11/2001 | Hancock | A61B 17/0206 606/167 |
| 2001/0041828 A1 * | 11/2001 | Deckman | A61B 17/0206 600/232 |
| 2002/0099269 A1 | 7/2002 | Martin et al. | |
| 2005/0159651 A1 | 7/2005 | Raymond et al. | |
| 2008/0140085 A1 * | 6/2008 | Gately | A61F 2/4465 606/99 |
| 2011/0130793 A1 * | 6/2011 | Woolley | A61B 17/7076 606/279 |
| 2012/0010472 A1 * | 1/2012 | Spann | A61F 2/447 600/214 |
| 2012/0271118 A1 * | 10/2012 | White | A61B 17/02 600/226 |
| 2013/0023735 A1 * | 1/2013 | Brown | A61B 90/50 600/229 |
| 2013/0204262 A1 * | 8/2013 | Menendez | A61B 17/02 606/89 |
| 2013/0345520 A1 | 12/2013 | Hamada | |
| 2014/0257039 A1 * | 9/2014 | Feldman | A61B 17/02 600/205 |
| 2014/0350347 A1 * | 11/2014 | Karpowicz | A61B 17/0206 600/215 |
| 2015/0018628 A1 * | 1/2015 | Friedrich | A61B 17/025 600/214 |
| 2015/0305731 A1 * | 10/2015 | Friedrich | A61B 17/0206 600/216 |
| 2016/0081818 A1 * | 3/2016 | Waugh | A61B 17/0206 623/17.16 |
| 2016/0354073 A1 * | 12/2016 | Nel | A61B 17/02 |
| 2017/0014117 A1 * | 1/2017 | Capote | A61B 17/0206 |
| 2017/0333023 A1 * | 11/2017 | Adams | A61B 17/0293 |
| 2018/0042595 A1 * | 2/2018 | Tsubouchi | A61B 17/0206 |
| 2019/0029497 A1 | 1/2019 | Mirza et al. | |
| 2019/0105179 A1 | 4/2019 | Spann | |
| 2020/0015799 A1 * | 1/2020 | Tsubouchi | A61B 17/0206 |

OTHER PUBLICATIONS

Office Action dated Nov. 5, 2021 in U.S. Appl. No. 17/108,882.
Office Action dated Feb. 1, 2022 in U.S. Appl. No. 17/155,903.

* cited by examiner

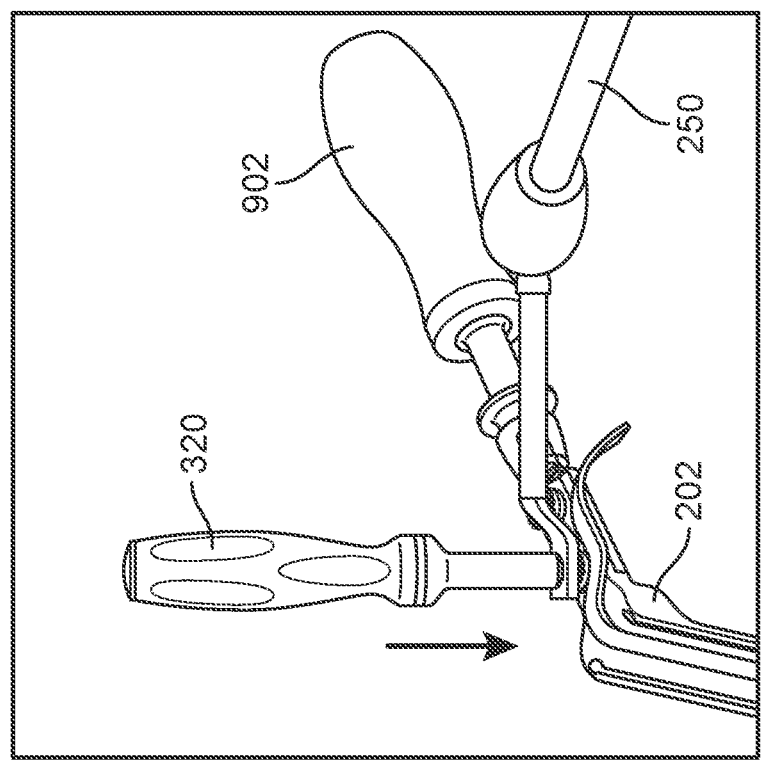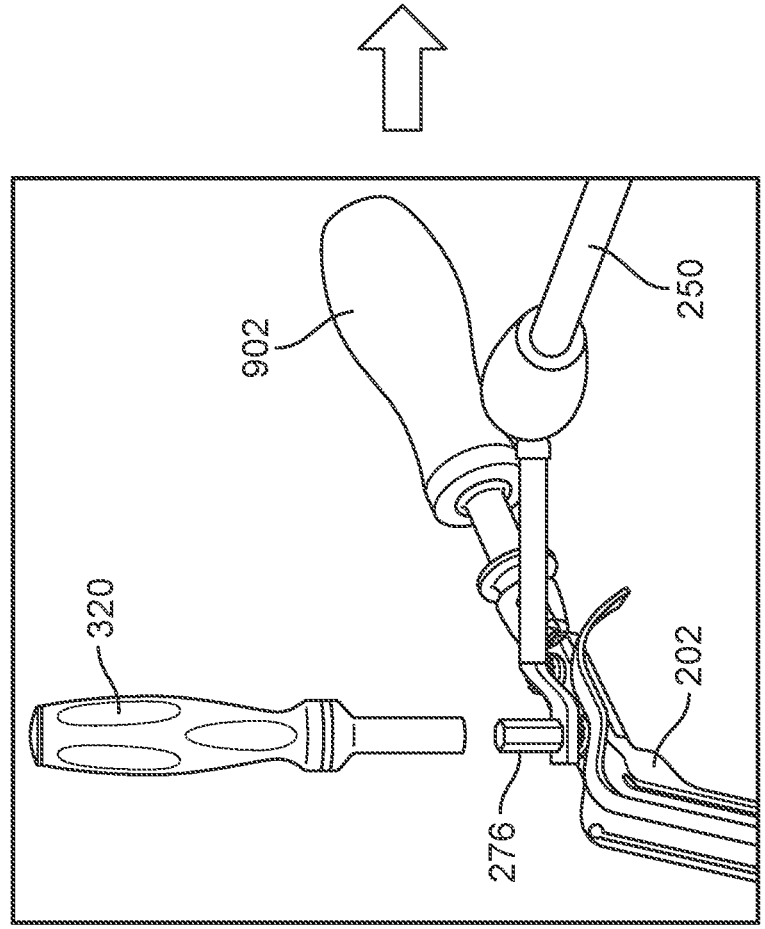
FIG. 11

MODULAR RETRACTOR SYSTEM AND METHOD OF USE

CROSS-REFERENCE TO RELATED APPLICATIONS

This application claims the benefit of Provisional Patent Application No. 62/939,143, filed on Nov. 22, 2019, and titled "MODULAR RETRACTOR SYSTEM," the entire disclosure of which is hereby incorporated by reference.

BACKGROUND

Retractor systems may be used in a variety of different surgical procedures to provide an opening through which the doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site using X-ray.

Retractor systems may include a plurality of blades. In use, the blades may be inserted into an incision and then retracted to displace tissue surrounding the incision, thereby exposing the surgical site. To minimize trauma to the tissue, this tissue displacement should be refined and controlled. However, current retractor systems do not provide desired control of the distraction. More particularly, the devices currently in use limit the ability of the surgeon to feel the resistance at the blades as tissue is being retracted. The devices currently in use also limit the surgeon's ability to position and rotate the blades independently. This limited control takes away the skilled surgeon's ability to finely adjust the movement of the retractor blades.

There is a need in the art for a system and method that addresses the shortcomings discussed above.

SUMMARY

In one aspect, a retractor system includes a first blade assembly comprising a first retractor blade. The system also includes a second blade assembly comprising a second retractor blade. The system also includes a table arm, the table arm including a first end and a second end, wherein the first end is configured to be secured in place adjacent an operating area. The system also includes a blade-to-blade articulating arm including a first end and a second end. The second end of the table arm can be fastened to the first retractor blade. The first end of the blade-to-blade articulating arm can be fastened to the first retractor blade. The second end of the blade-to-blade articulating arm can be fastened to the second retractor blade.

In another aspect, a retractor system includes a first retractor blade, a second retractor blade, and a third retractor blade. The system also includes a table arm, the table arm including a first end and a second end, where the first end is configured to be secured in place adjacent an operating area. The system also includes a first blade-to-blade articulating arm including a first end and a second end and a second blade-to-blade articulating arm including a first end and a second end. Each of the first retractor blade, the second retractor blade and the third retractor blade comprise two connectors. An end of the table arm is configured to fasten to a first connector of the first retractor blade. A first end of the first blade-to-blade articulating arm is configured to fasten to a second connector of the first retractor blade. A second end of the first blade-to-blade articulating arm is configured to fasten to a first connector of the second retractor blade. A first end of the second blade-to-blade articulating arm is configured to fasten to a second connector of the second retractor blade. A second end of the second blade-to-blade articulating arm is configured to fasten to a connector of the third retractor blade.

In another aspect, a method of positioning a retractor system within a body includes steps of inserting a first retractor blade into an incision in the body and inserting a second retractor blade into the incision after the first retractor blade has been inserted, where the second retractor blade can be positioned independently of the first retractor blade. The method also includes steps of coupling an end of a table arm to the first retractor blade, inserting a third retractor blade into the incision after the first retractor blade and the second retractor blade have been inserted, coupling a first end of a first blade-to-blade articulating arm to the first retractor blade and coupling a second end of the first blade-to-blade articulating arm to the third retractor blade, coupling a first end of a second blade-to-blade articulating arm to the third retractor blade, and coupling a second end of the second blade-to-blade articulating arm to the second retractor blade.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

FIG. 11 is a schematic view of fastening tool being used to couple an end of a table arm to a retractor blade, according to an embodiment;

DETAILED DESCRIPTION

Figure 1:
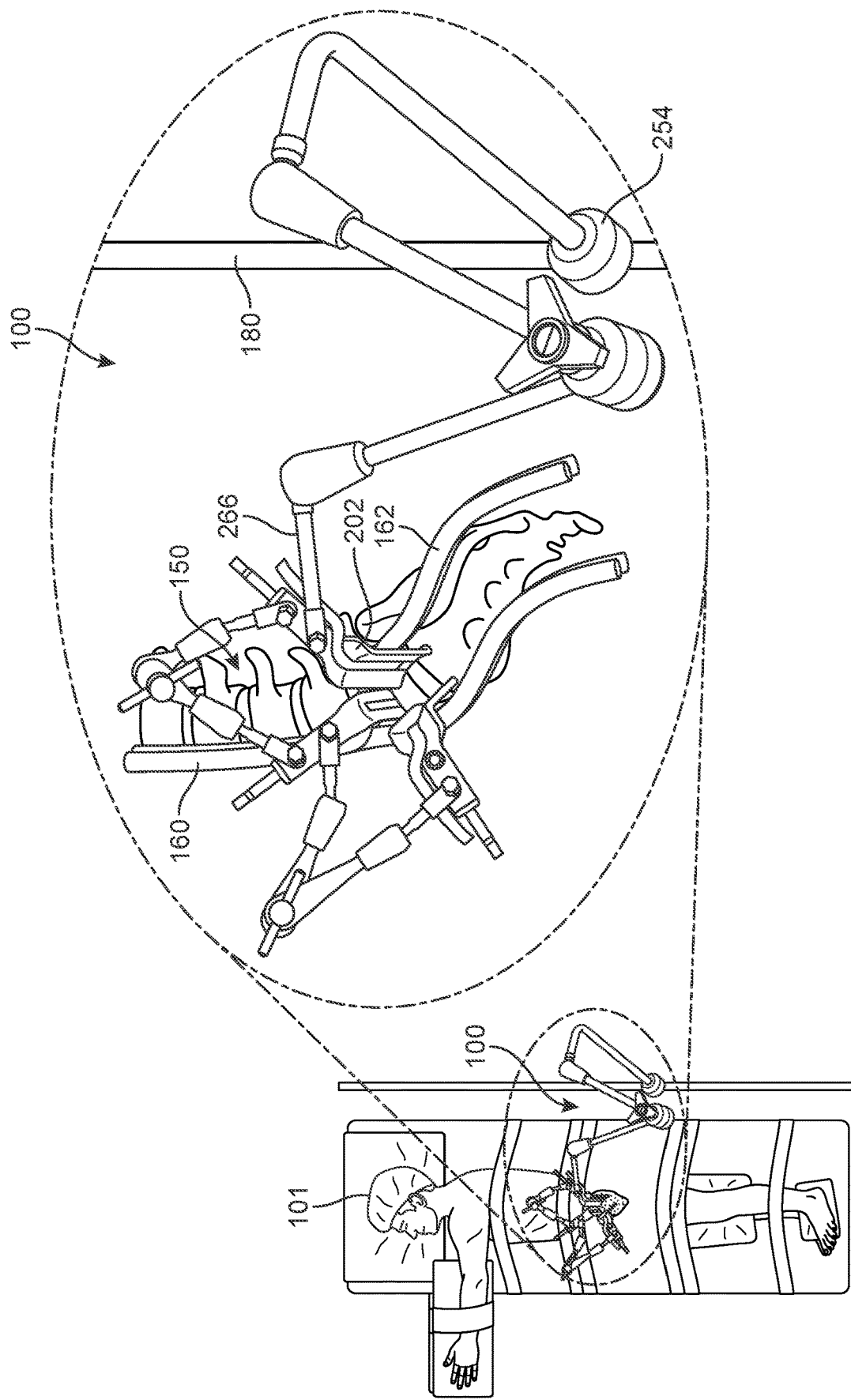
FIG. 1 is a schematic view of a modular retractor system in use during a surgical procedure, according to an embodiment.

The embodiments described herein are directed to a modular retractor system and its method of use. The modular retractor system comprises a set of retractor blades that can be used to retract soft tissue and anatomical features in preparation for a surgical procedure. The blades can be independently inserted and positioned adjacent a surgical site and then coupled together using one or more blade-to-blade articulating arms. One or more blades can also be coupled to a fixed structure, such as a surgical table, using a table arm which locks the position of the blade in place relative to the fixed structure.

Each retractor blade can be attached to a releasable handle. A surgeon can insert and manipulate the position of the retractor blade easily using the releasable handle. This enables the surgeon to receive important tactile feedback, reducing the chances of tissue damage caused by imprecise manipulation of the blades. Moreover, since each blade is positioned independently before it is fixed in place relative to the other blades, blade placement is not constrained to fixed spatial configurations, such as positions along a fixed ring or rectangle. Instead, each blade can be placed in an ideal location that is compatible with the particular patient's anatomy before the blades are securely fixed in place and locked to the operating table.

Because the blade-to-blade articulating arms provide a rigid connection between the blades, this eliminates the need for more than one table arm in the surgical area and reduces the need for additional assistance in holding the blades in place.

The embodiments describe a particular use of the modular retractor system in preparing an incision for oblique lateral interbody fusion (or OLIF) spinal surgery. OLIF is a less invasive approach to spinal fusion surgery in which the surgeon accesses and repairs the lower (lumbar) spine from the front and side of the body (passing in a trajectory about halfway between the middle of the stomach and the side of the body). During an OLIF procedure, the surgeon uses a corridor between the psoas muscle and the peritoneum to access the spine. The psoas muscles connect the lower back to the thighs and enable movement and flexibility of the back, pelvis, legs, and hips. The peritoneum is the membrane that lines the abdominal cavity.

Although the embodiments describe a particular configuration of the retractor system for use with OLIF procedures, it may be appreciated that the retractor system could be used for retracting skin and other tissue during other types of suitable surgeries. Moreover, for use in other kinds of surgeries, in some cases, the linkages between the blades as well as the specific configuration of blades themselves could vary from the configurations described below.

The terms "proximal" and "distal" may be used in the description. As used herein, proximal means closer a surgeon or person holding a component, while distal means further from the surgeon or person holding the component. Likewise, the terms "posterior" and "anterior" may be used in the description. A structure (part, portion, etc.) is anterior to another structure when it is closer to the front of the body. A structure that is posterior to another is closer to the back of the body.

FIG. 1 is a schematic view of a patient undergoing surgery. Specifically, patient 101 is undergoing a spinal fusion procedure that uses the oblique lumbar interbody fusion (OLIF) approach. In this particular example, the patient is undergoing surgery at the L5-S1 spinal motion segment, also known as the lumbosacral joint. As shown in an enlarged focal view within FIG. 1, a retractor system 100 is being used to retract soft tissue and anatomical features in preparation for the procedure. Also visible in FIG. 1 is a segment 150 of the spinal column, which includes portions of the lumbar spine and the sacral spine in the lower back. For purposes of illustration, a portion of the vascular system 160 is also shown in FIG. 1, as OLIF surgery typically requires mobilization of at least some portions of this system, such as the iliac and femoral arteries. For reference, the left common femoral artery is indicated in FIG. 1 as artery 162.

Figure 2:
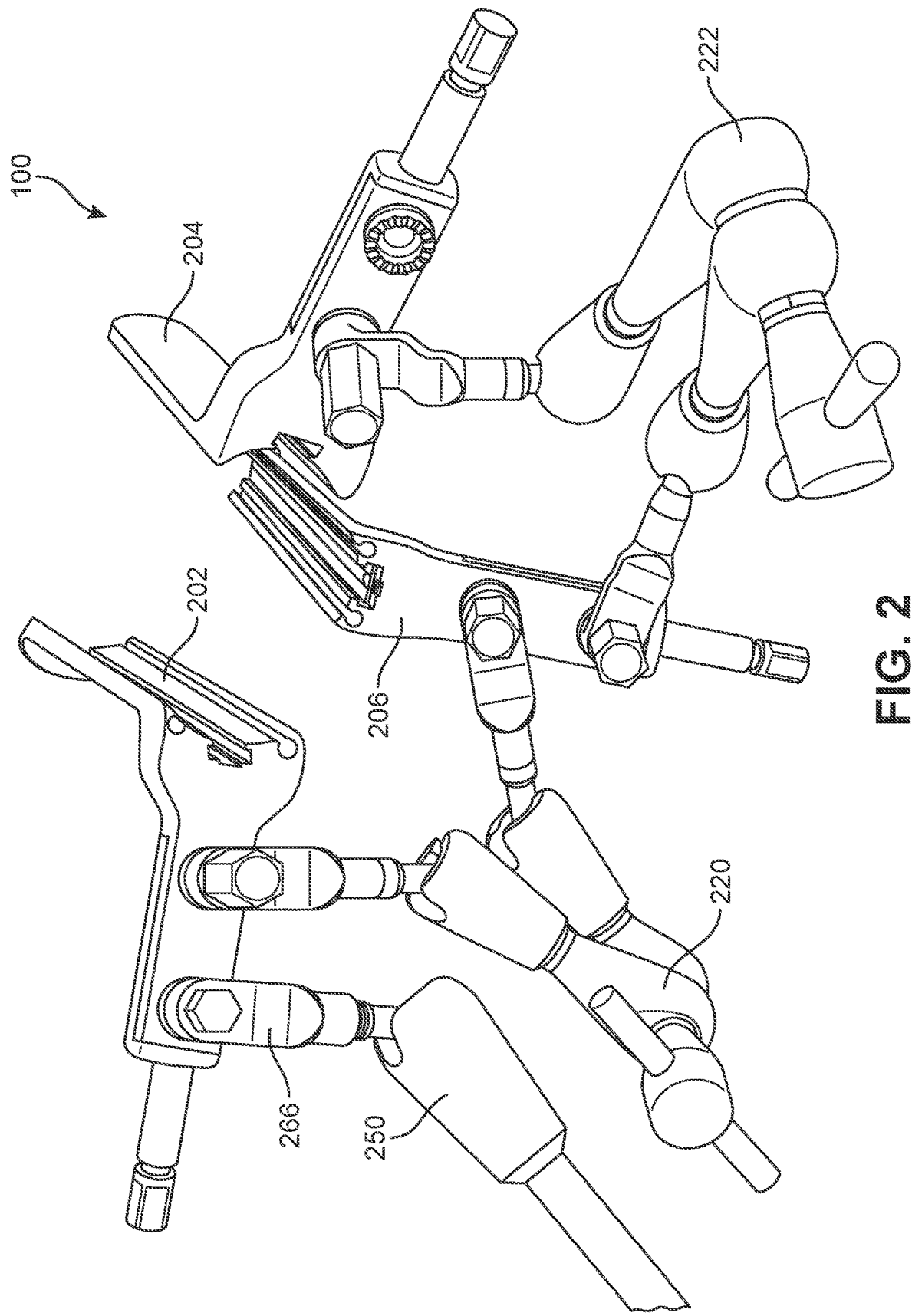
FIG. 2 is a schematic view of a modular retractor system, according to an embodiment.

FIG. 2 is a schematic view of retractor system 100 shown in isolation. Additionally, FIG. 3 shows a schematic top down view of the various components that may comprise retractor system 100 in a disassembled configuration.

Figure 3:
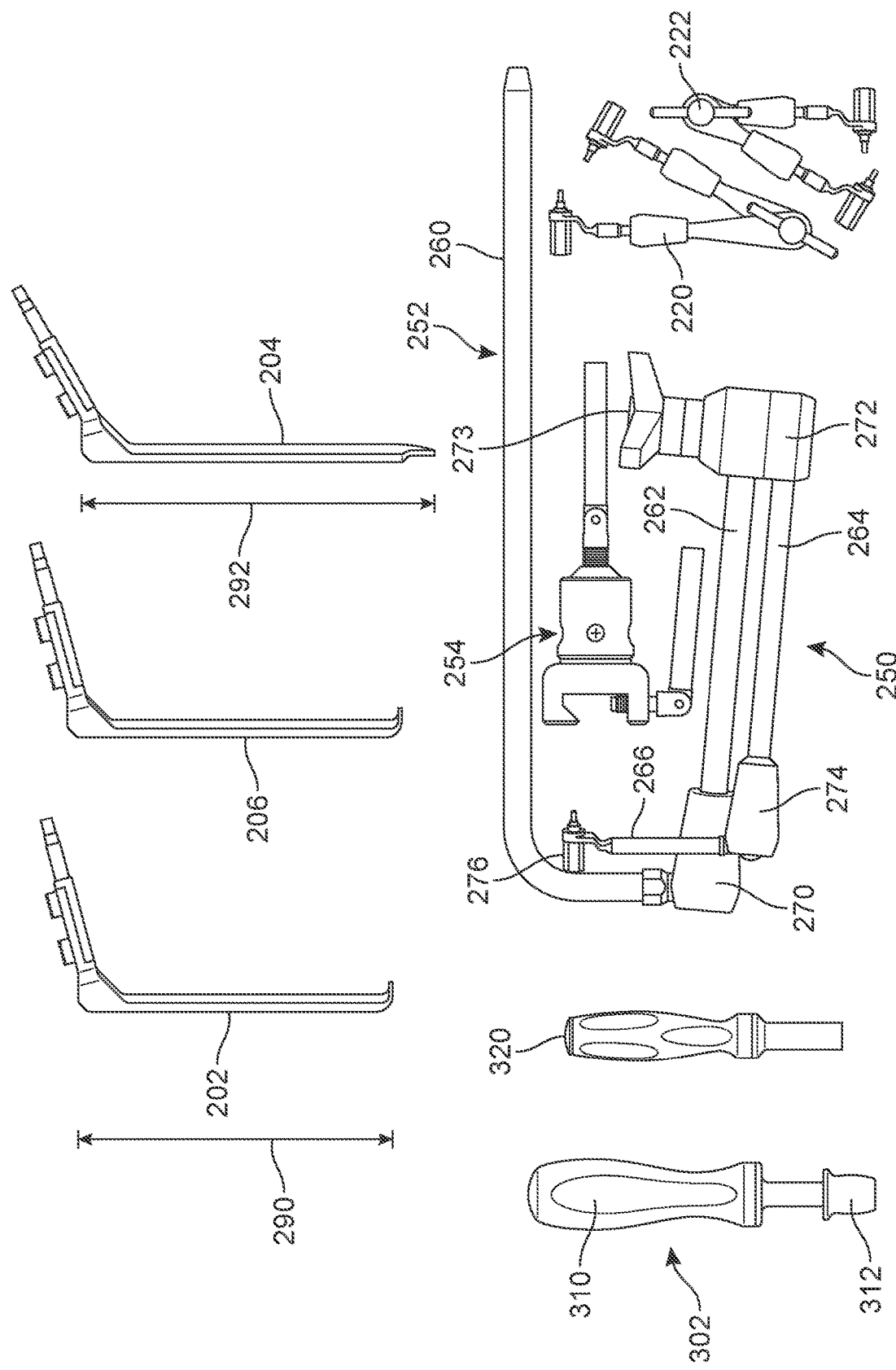
FIG. 3 is a schematic disassembled view of multiple components that comprise a modular retractor system, according to an embodiment.

Referring now to FIGS. 2 and 3, retractor system 100 may include one or more retractor blades. In the illustrated embodiment, retractor system 100 includes a first retractor blade 202, a second retractor blade 204, and a third retractor blade 206. Together, the three retractor blades may be used to retract opposing sides of an incision, as well as to mobilize distinct portions of the anatomy, thereby creating an opening for an oblique lateral approach to the lumbar spine. As discussed in further detail below, the ends of each blade may be curved or otherwise shaped in a manner that assists in retraction of soft tissue and/or bone. For example, some retractor blades could be vein retractors, which tend to have flanged or curled ends that can be used to displace veins or other soft tissue. Other retractor blades could be Hohmann retractors, which may have a rounded tip that facilitates positive engagement with the bone.

In the exemplary configuration, each of the three retractor blades may be utilized for a particular function in preparing the surgical site for an OLIF procedure. For example, first retractor blade 202 may be designed for placement medially of the left common iliac vein, for a left sided up approach, or medially of the right common iliac vein/artery, for a right sided up approach. Second retractor blade 204 may be designed for placement medially for the right common iliac vein/artery, for a left sided up approach, or medially of the left common iliac vein/artery for a right sided up approach. Third retractor blade 206 may be designed for placement caudally of the bifurcation of the veins/arteries.

Retractor system 100 may be further comprised of components for attaching blades to one another in a manner that fixes the relative positions of the blades in a substantially rigid manner. In the illustrated embodiment, as shown in FIG. 2, retractor system 100 includes a first blade-to-blade articulating arm 220 and a second blade-to-blade articulating arm 222. As further shown in FIG. 2, first blade-to-blade articulating arm 220 is seen to connect first retractor blade 202 with third retractor blade 206. Likewise, second blade-to-blade articulating arm 222 is seen to connect second retractor blade 204 with third retractor blade 206.

To keep the retractor blades in an absolute fixed position, relative to the operating table, another articulating assembly may be used. For example, as seen in FIG. 3, a table arm 250 could be used. Unlike the blade-to-blade articulating arms, table arm 250 may be used to connect a blade to a fixed structure in the operating area. Examples of fixed structures include, but are not limited to: operating tables, guide rails (on a bed or table), and/or any other structure in an operating area whose position is fixed during the procedure.

Table arm 250 may comprise an articulating arm portion 252 and a clamp portion 254. Articulating arm portion 252 may further comprise a base segment 260, a first articulating segment 262, a second articulating segment 264, and a fastening segment 266. When assembled, the free end of segment 260 may be attached directly to clamp portion 254.

First articulating segment 262 may be coupled to base segment 260 by a ball-and-socket connector 270, thereby allowing first articulating segment 262 to articulate relative to base segment 260, as the position and orientation of the latter may be fixed relative to clamp portion 254. Second articulating segment 264 may be coupled to first articulating segment 262 by a rotating connector 272. As seen in FIG. 3, rotating connector 272 may include a handle 273 that can be used to tighten the connection and lock the rotational angle between the adjacent articulating segments.

Fastening segment 266 may be coupled to second articulating segment 264 by another ball-and-socket connector 274. Fastening segment 266 may further include a fastener 276, which can be connected to corresponding fasteners on the retractor blades as discussed in more detail below.

Referring again to FIG. 1, table arm 250 can be fixed at a first end to a rail 180 of an operating table via clamp portion 254. Clamp portion 254 may be any type of mechanism suitable for removably securing table arm 250 to rail 180. Fastening segment 266 can be fastened to a retractor blade (e.g., retractor blade 202), thereby holding the blade in a fixed position relative to rail 180. The connection between fastening segment 266 and retractor blade 202 can be better seen in FIG. 2. (For purposes of illustration, only a portion of table arm 250 is shown in FIG. 2.)

Although the exemplary embodiment shows a system comprised of three blades, in other embodiments only two blades could be used to retract an incision for a surgical procedure. In such an embodiment, the system may require only one blade-to-blade articulating arm to connect the two blades. Likewise, in still other surgical procedures, three or more blades could be used. When three or more blades are used, additional blade-to-blade articulating arms could be used to connect the additional blades to one of the first two blades.

To facilitate positioning the retractor blades, the system may include a releasable handle for each blade. Once the retractor blade(s) are positioned, one or more of the releasable handles may be removed, e.g., via quick connect connections, from the blades in order to reduce clutter in the operating field.

As seen in FIG. 3, a retractor system can also include a releasable handle 302. Releasable handle 302 may be releasably attached to a retractor blade (such as first blade 202, second blade 204, or third blade 206). Releasable handle 302 may itself be further comprised of a grasping portion 310 and a connector portion 312. In one embodiment, releasable handle 302 may be a quick connect (QC) handle that utilizes a quick connection fastening system. Although a single releasable handle 302 is shown in FIG. 3, it may be appreciated that each blade may be configured with its own releasable handle.

To assist in fastening the components of a retractor system to one another, a fastening tool such as hex driver 320 could be used, as described in further detail below. For purposes of clarity a single hex driver is shown in FIG. 3, however in other embodiments two or more different hex drivers may be used with a retractor system. In some embodiments, such a hex driver tool may be included with a kit of parts including all of the retractor components.

Figure 4:
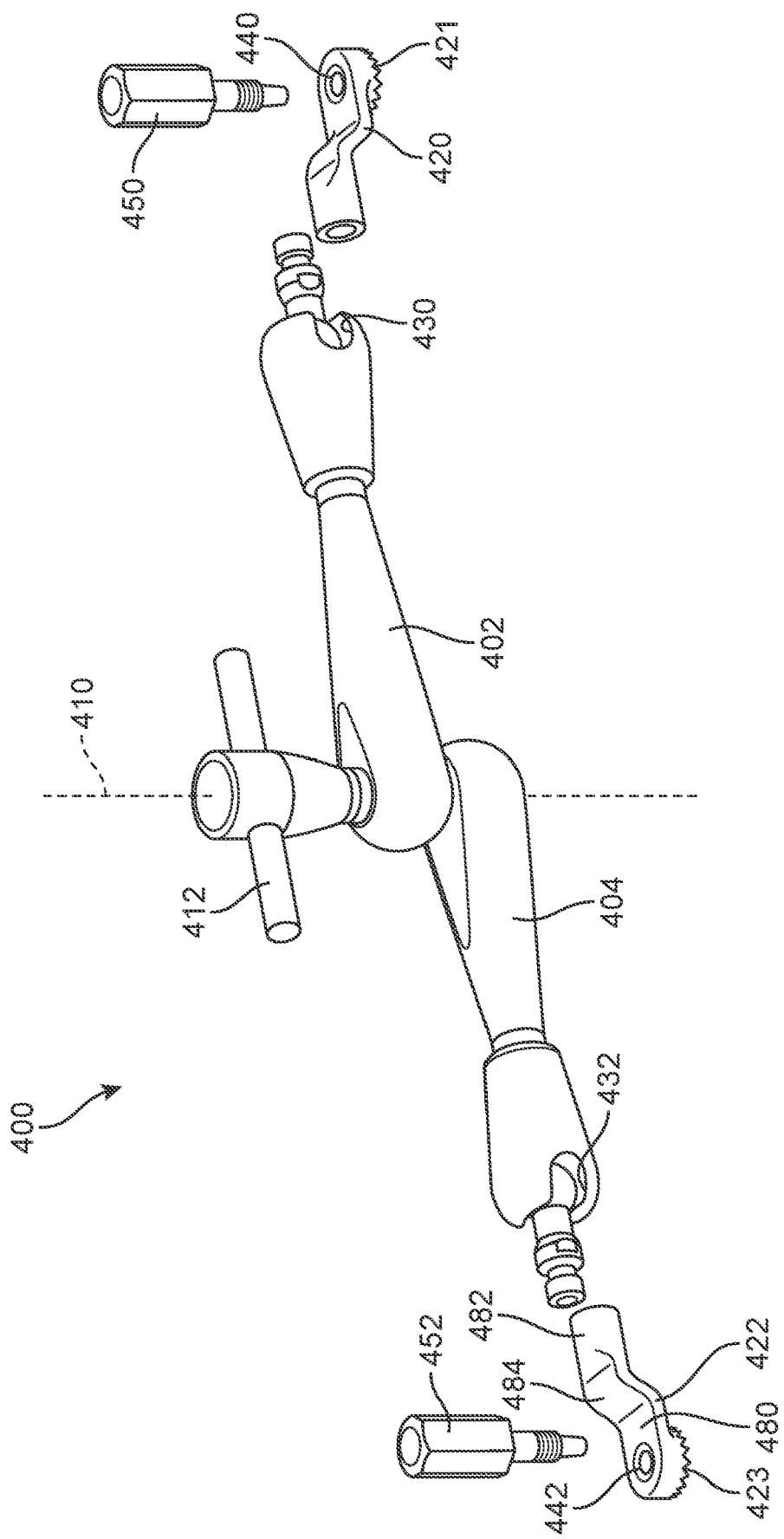
FIG. 4 is a schematic view of a blade-to-blade articulating arm, according to an embodiment.

FIG. 4 is a schematic view of a blade-to-blade articulating arm 400 ("assembly 400"). Referring to FIG. 4, assembly 400 may comprise a first segment 402 and a second segment 404. First segment 402 and second segment 404 may overlap at corresponding inward ends (that is, ends located towards the center of the assembly). Moreover, these segments may be connected in a manner that facilitates rotation about a common axis 410. A rotating handle 412 also rotates about the same common axis 410 and allows the rotational angle between the segments to be locked into place when tightened.

The outward ends of each segment include a blade-engaging connector that is pivotally connected to the segment by a ball-and-socket connector. Specifically, first segment 402 is attached at its outward end to a first blade-engaging connector 420 ("connector 420") by way of a first ball-and-socket connector 430. Likewise, second segment 404 is attached at its outward end to a second blade-engaging connector 422 ("connector 422") by way of a second ball-and-socket connector 432. To better illustrate the nature of the ball-and-socket connection, each blade-engaging connector is shown as exploded from its corresponding ball-and-socket connector. However, it may be appreciated that each blade-engaging connector may be fixedly attached to the male end of the associated ball-and-socket connector.

Each blade-engaging connector is configured with a ring of teeth that can engage corresponding teeth on one or more blades. Specifically, first connector 420 includes a ring of teeth 421, while second connector 422 includes a ring of teeth 423.

Each blade-engaging connector is also associated with a threaded fastener. For example, first connector 420 includes a first opening 440 that receives a first threaded fastener 450. Likewise, second connector 422 includes a second opening 442 that receives a second threaded fastener 452. These threaded fasteners are used to secure the first and second blade-engaging connectors to the retractor blades, as described below and shown, for example, in FIGS. 12-14.

As seen in FIG. 4, each of first connector 420 and second connector 422 has an inward portion, an outward portion, and a curved intermediate portion. For example, second connector 422 may include an outward portion 480, an inward portion 482, and an intermediate portion 484. The outward portion includes teeth for engaging a blade and the inward portion includes an opening to receive a projection from a corresponding ball-and-socket connector. The curved intermediate portion creates a step-down like geometry between the outward and inward portions. This configuration may provide sufficient clearance between the articulating arm and a connector on a retractor blade. Specifically, when the outward end of the connector is attached to a first connector on a retractor blade, the inward end may be displaced away from the blade by a sufficient vertical distance so that the inward end does not come into contact with a second connector on the blade, even as the arm is pivoted about the first connector prior to tightening the connection.

Figure 5:
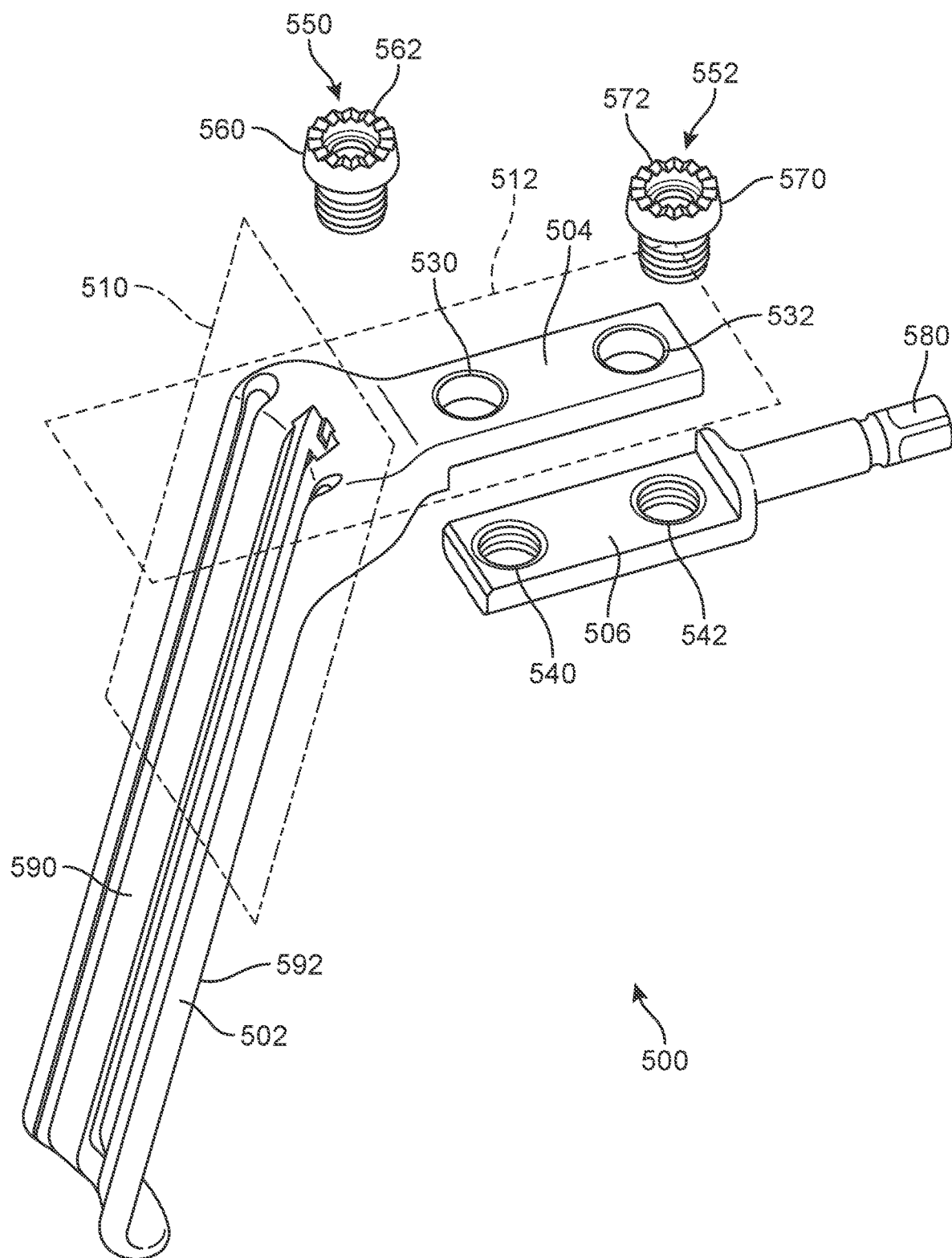
FIG. 5 is a schematic exploded view of a retractor blade, according to an embodiment.

FIG. 5 is a schematic exploded view of an embodiment of a retractor blade 500. In this embodiment, retractor blade 500 may itself be comprised of a blade portion 502, a mounting portion 504, and a releasable connector portion 506.

Blade portion 502 may be substantially straight along its length and may include a first side 590 and a second side 592. The first side may define a first direction that extends away from the first side and which is normal to the first side. The second side may define a second direction that extends away from the second side and which is normal to the second side.

Mounting portion 504 may be continuously formed with blade portion 502, however mounting portion 504 may have a different orientation from blade portion 502. For example, in the embodiment of FIG. 5, a planar surface 510 associated with the length and width of blade portion 502 may be disposed at an angle to a planar surface 512 associated with the length and width of mounting portion 504. Here, mounting portion 504 is seen to extend away from second side 590 of blade portion 502. Because the mounting portion is oriented along the direction of the handle, this orientation for mounting portion 504 relative to blade portion 502 allows a surgeon to better grasp and manipulate the retractor blade as it is inserted into the body.

Mounting portion 504 may comprise two fastener openings: a first fastener opening 530 and a second fastener opening 532. Each opening may overlap with a corresponding opening on releasable connector portion 506. Specifically, fastener opening 530 may correspond to a fastener opening 540 in releasable connector portion 506, while fastener opening 532 may correspond to a fastener opening 542 in releasable connector portion 506. These openings may further receive a first threaded connector 550 (through fastener opening 530 and fastener opening 540) and a second threaded connector 552 (through fastener opening 532 and fastener opening 542). Each connector includes threading that can engaging corresponding threading in the openings of releasable connector portion 506. When fastened into place, these connectors secure releasable connector portion 506 to mounting portion 504.

Additionally, each connector includes a ring comprised of teeth. Specifically, first connector 550 includes an outer ring 560 that is comprised of teeth 562. Likewise, second connector 552 includes an outer ring 570 that is comprised of teeth 572. The teeth of each connector are configured to engage corresponding teeth in one or more of the articulating arms (such as teeth 421 or teeth 423 shown in FIG. 4).

As seen in FIG. 5, releasable connector portion 506 includes a quick connect end 580 that is sized and shaped to mate with a corresponding opening in a quick connect handle (such as handle 302 of FIG. 3).

Figure 6:
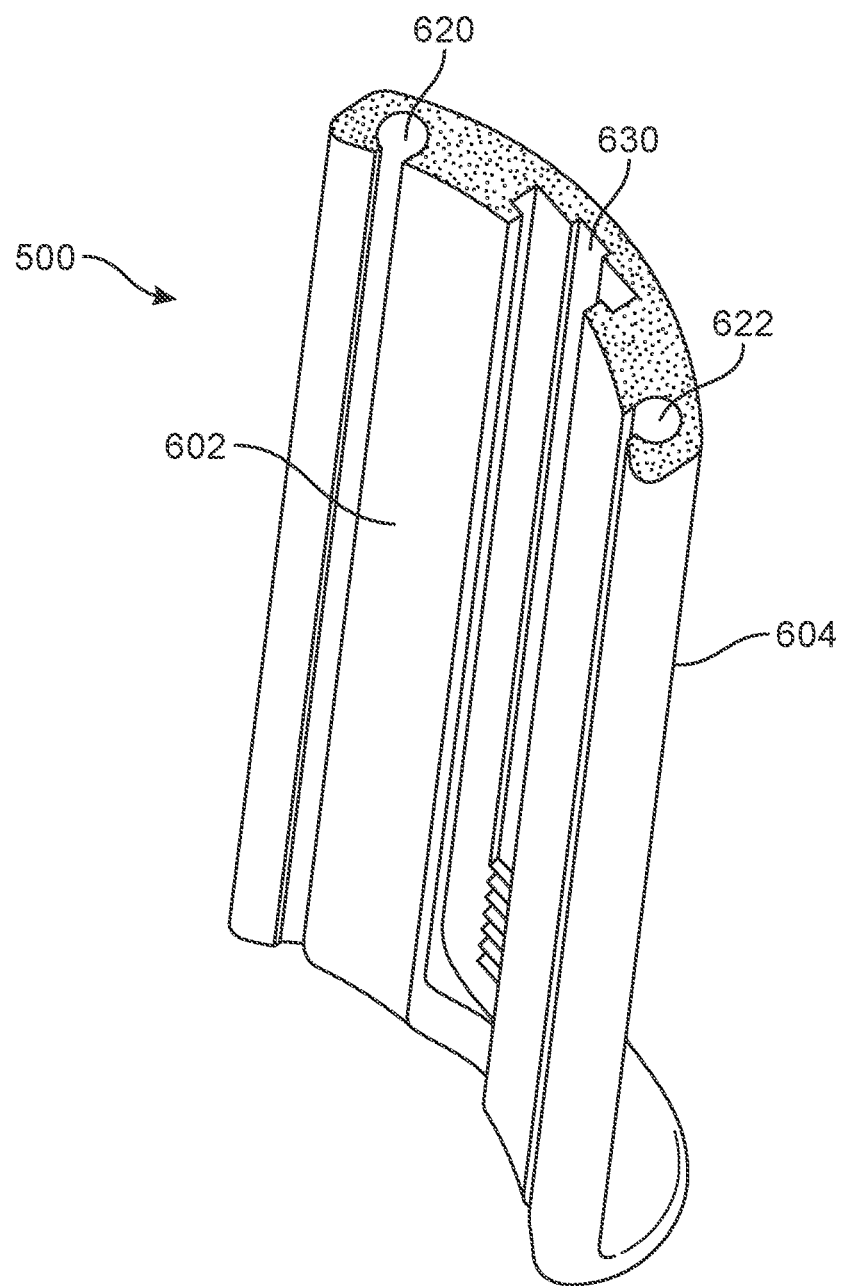
FIG. 6 is a schematic cut-away view of a portion of a retractor blade, according to an embodiment.

FIG. 6 is a schematic perspective cross-sectional view of a portion of retractor blade 500. Referring to FIG. 6, retractor blade 500 may include a first surface 602 and an opposing second surface 604. When inserted into the body, second surface 604 may be placed against soft tissue and/or bone in order to retract or pull at the tissue. First surface 602 may face inwardly towards a cavity created inside the body by the use of two or more retractor blades. In some cases, the body of retractor blade 500 may be curved so that first surface 602 takes on a concave geometry, while second surface 604 takes on a convex geometry. The curvature of retractor blade 500 may help provide additional strength and support over a substantially flat blade. Additionally, when used in conjunction with other concave blades, the concavity of the blades provides an enlarged opening through which the surgery may be performed. Further, the convex geometry of second surface 604 may be more gentle to tissue being retracted.

Along first surface 602, retractor blade 500 may further include two slots for receiving fixation pins (such as Steinman pins), K wires, or other devices used for fixation. Specifically, retractor blade 500 may include a first slot 620 adjacent one edge, and a second slot 622 adjacent the other edge.

First surface 602 can further include a T-shaped channel 630 that runs through the center of the blade along a lengthwise direction. Channel 630 may accommodate an illumination device. For example, in FIG. 7 an illumination device 750 can be seen extending through channel 630. Illumination device 750 could be a strip-like device that provides illumination, allowing a surgeon to better visualize the area where the blade has been inserted. Using a channel inside the surface of the blade allows the illumination device to be integrated into the blade without the illumination device protruding from the blade's surface, possibly impacting adjacent tissue. In one embodiment, the illumination device comprises a sheath or segment of malleable aluminum, so that once inserted to the desired position within channel 630, the proximal end of the illumination device may be bent back to help keep the device in place and out of the way of the surgeon.

It may be appreciated that one or more blades in a retractor system could include slots for fixation devices (like pins) and/or channels for illumination devices. In the exemplary embodiment, both first blade 202 and third blade 206 are configured with these slots and channels, as seen in FIG. 2.

Figure 8:
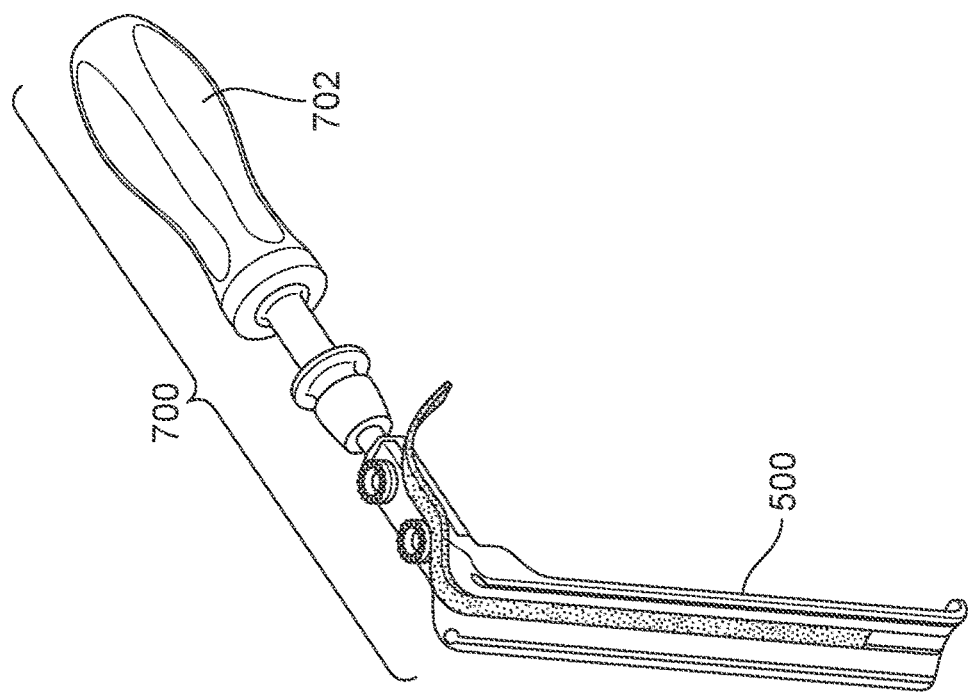
FIG. 8 is a schematic view of a retractor blade assembly in a coupled configuration, according to an embodiment.
Figure 7:
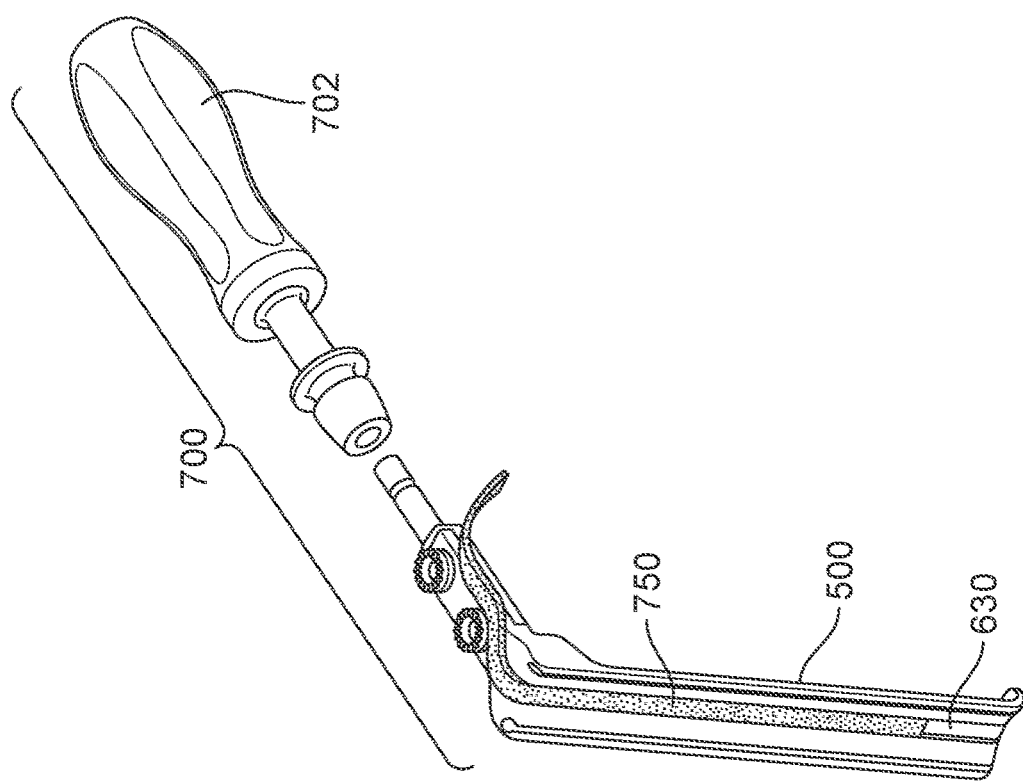
FIG. 7 is a schematic view of a retractor blade assembly in an uncoupled configuration, according to an embodiment.

FIGS. 7 and 8 depict configurations of retractor blade 500 and a corresponding releasable handle 702, which are collectively referred to as blade assembly 700. Specifically, FIG. 7 shows retractor blade 500 disconnected from releasable handle 700, while FIG. 8 shows retractor blade 500 connected to releasable handle 700. By using a quick connection between the blade and handle, a surgeon can easily remove the handle once the blade has been placed in the desired position, thereby helping clear the operative area of unnecessary components. This also reduces any chance that the handles may interfere with the placement of one or more articulating arms (either the blade-to-blade arms or the table arm).

FIGS. 9-21 depict schematic views of a procedure for assembling the retractor system at a surgical site in a manner that allows each blade to be individually inserted and positioned by a surgeon before the relative positions of the blades are fixed with respect to one another. For purposes of clarity, the exemplary procedure describes a process for inserting and assembling the retractor system in preparation for an OLIF surgical procedure. However, it may be appreciated that similar steps could be performed in preparing different parts of the body for other kinds of procedures. For purposes of illustration, only the components of retractor system 100 are shown, however it may be appreciated that the components are inserted, moved, and connected by a surgeon and/or surgical assistant(s).

Figure 9:
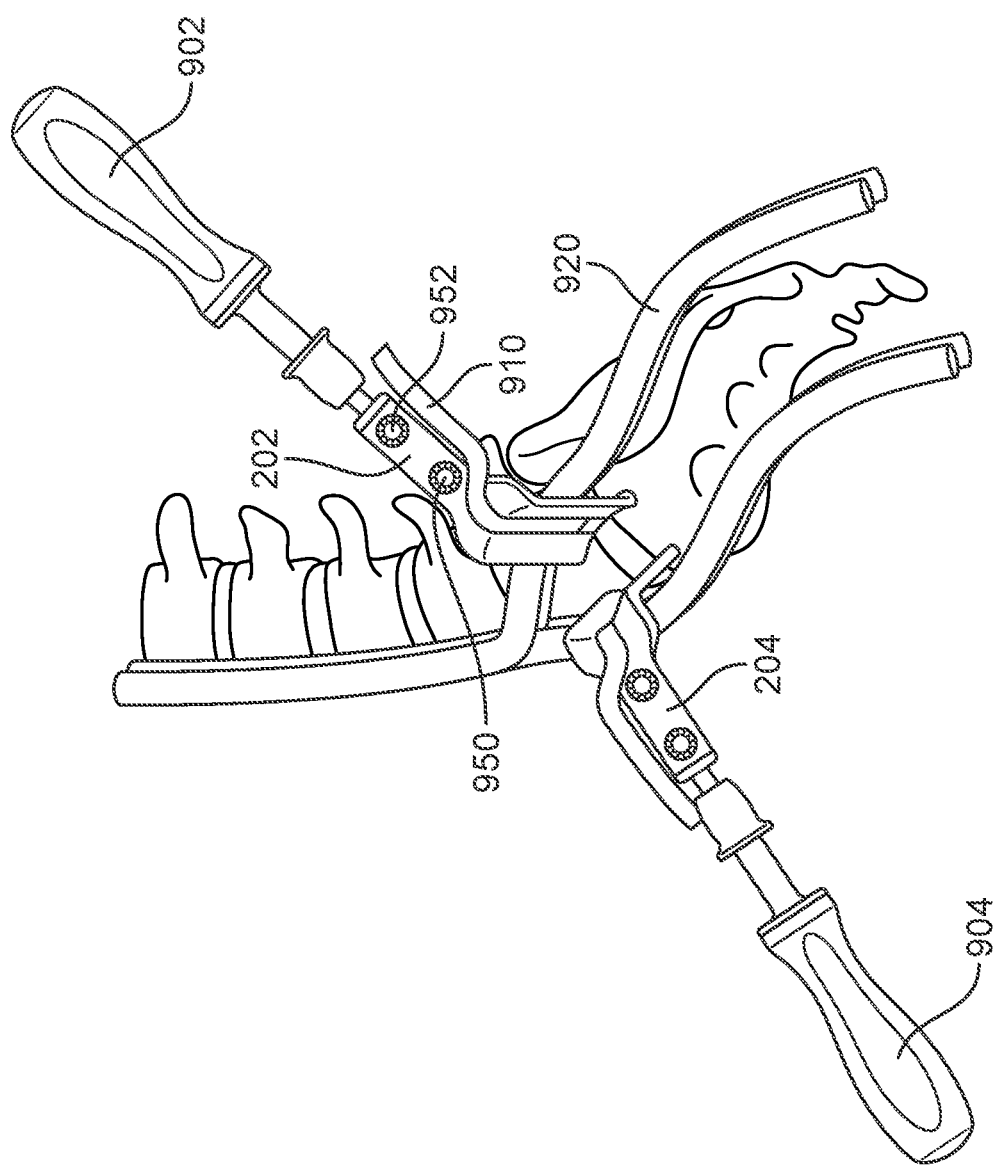
FIG. 9 is a schematic view of two retractor blades inserted adjacent a segment of the spine, according to an embodiment.

After an incision has been made and dissection to the spinal segment of interest (such as the L5-S1 segment) is completed, a surgeon may insert first retractor blade 202 and second retractor blade 204 into the incision area, as seen in FIG. 9. In some cases, an illumination device 910 may be used with first retractor blade 202 to more easily identify the L5-S1 disc via direct visualization. As seen in FIG. 9, first retractor blade 202 is coupled to releasable handle 902, and second retractor blade 204 is coupled to releasable handle 904. Using these handles facilitates easier blade manipulation for the surgeon.

Upon insertion, second blade 204 may be used to retract the medial aspect of the incision (not shown) and first blade 202 may be used to retract the lateral aspect of the incision. Moreover, first blade 202 may be placed on the medial or inner aspect of the left common femoral (artery 920) artery to ensure there are no peritoneal contents between the blade and the L5-S1 disc. Second blade 204, meanwhile, may be used to gently mobilize the prevertebral fascia over the L5-S1 disc space.

Figure 10:
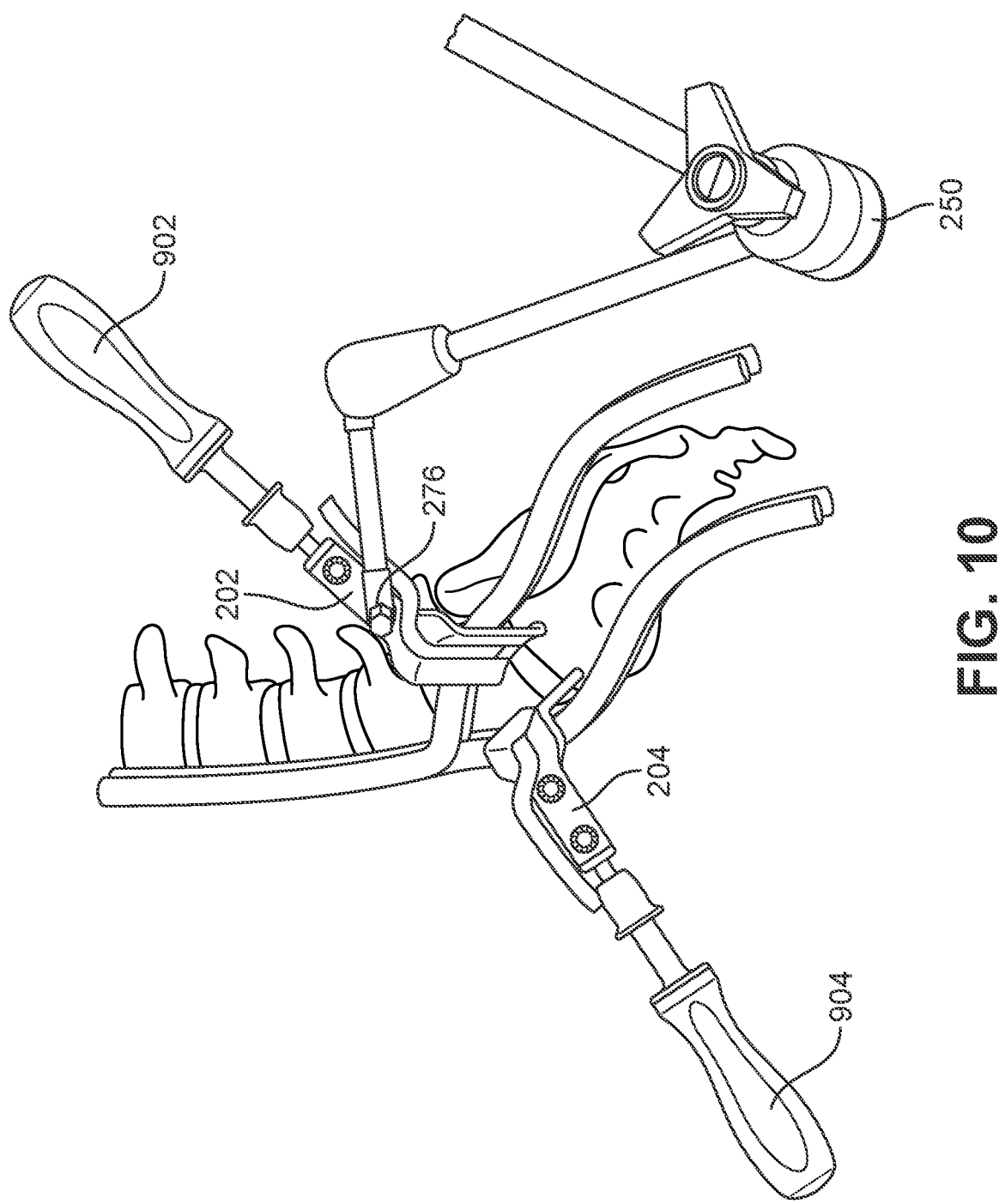
FIG. 10 is a schematic view of an end of a table arm being coupled to a retractor blade, according to an embodiment.

With the two blades inserted, first blade 202 can be provisionally attached to table arm 250, which may have been previously clamped to a rail or other fixed structure. As seen in FIG. 10, table arm 250 can be attached to first blade 202 by placing fastener 276 over a corresponding connector on first blade 202.

As shown in FIG. 9, first retractor blade 202 can include first connector 950 and second connector 952. Fastener 276 can be attached to first connector 950 of first retractor blade 202 by either hand tightening fastener 276 or by using a fastening tool. In the example shown in FIG. 11, hex driver 320 may be used to tighten fastener 276. Hex driver 320 may include an opening at its end that engages the hexagonal shaped body of fastener 276.

Figure 12:
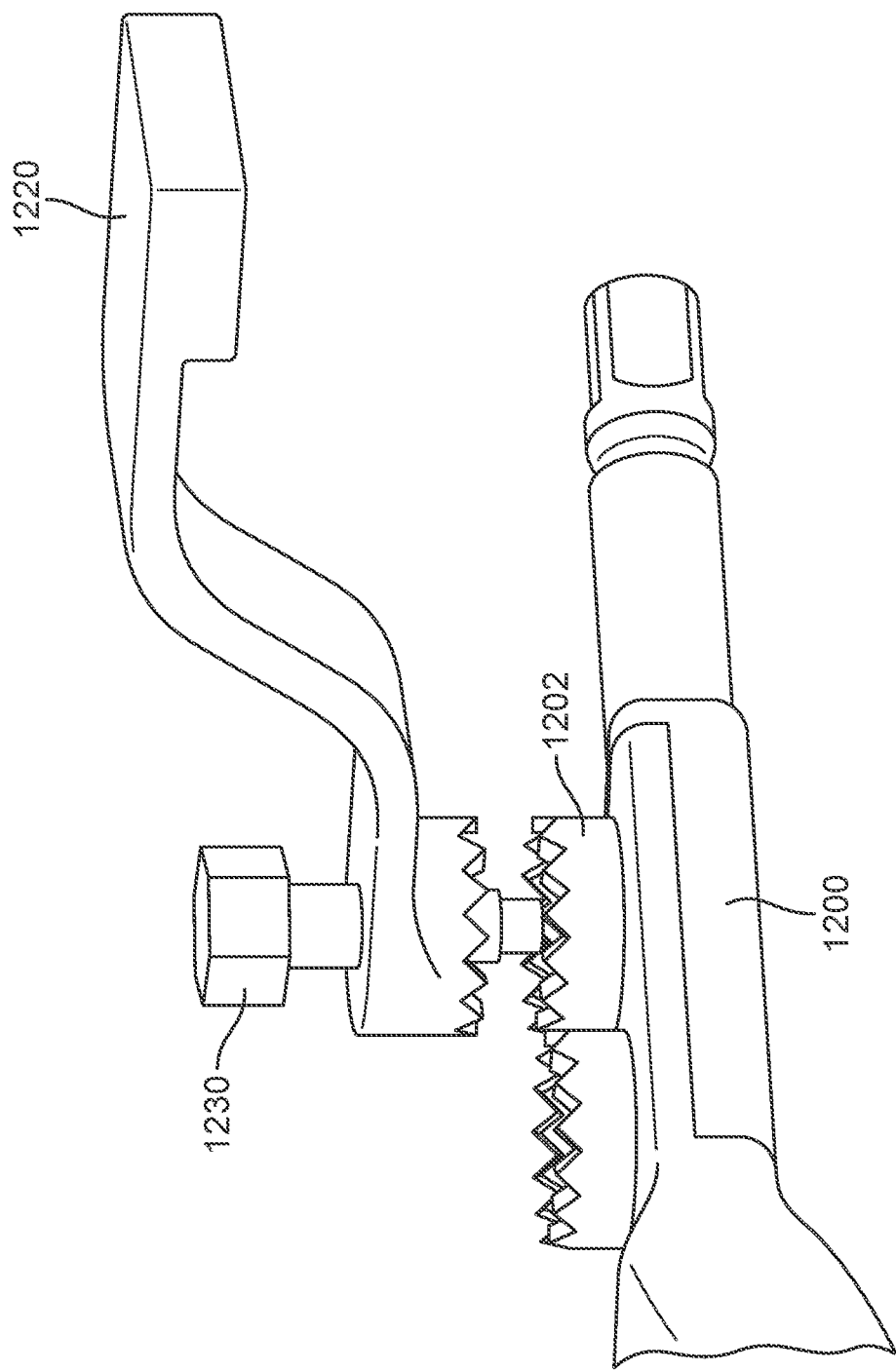
FIG. 12 is a schematic perspective view of a connecting portion of a table arm being partially fastened to a retractor blade, according to an embodiment.
Figure 13:
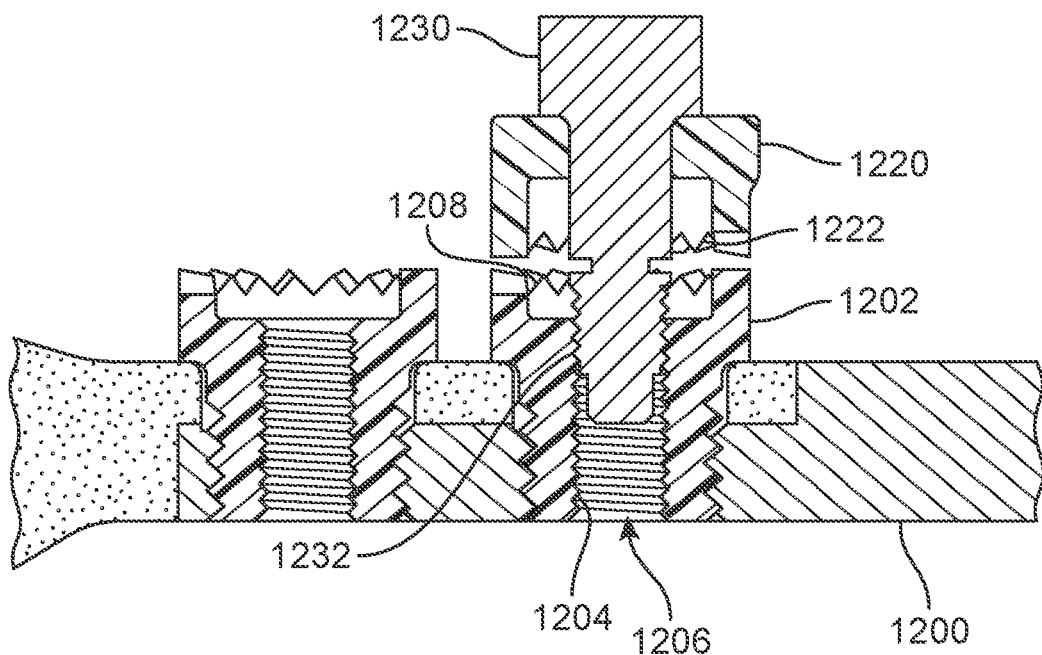
FIGS. 13-14 are schematic cross-sectional views of a connecting portion of a table arm being fastened to a retractor blade, according to an embodiment.
Figure 14:
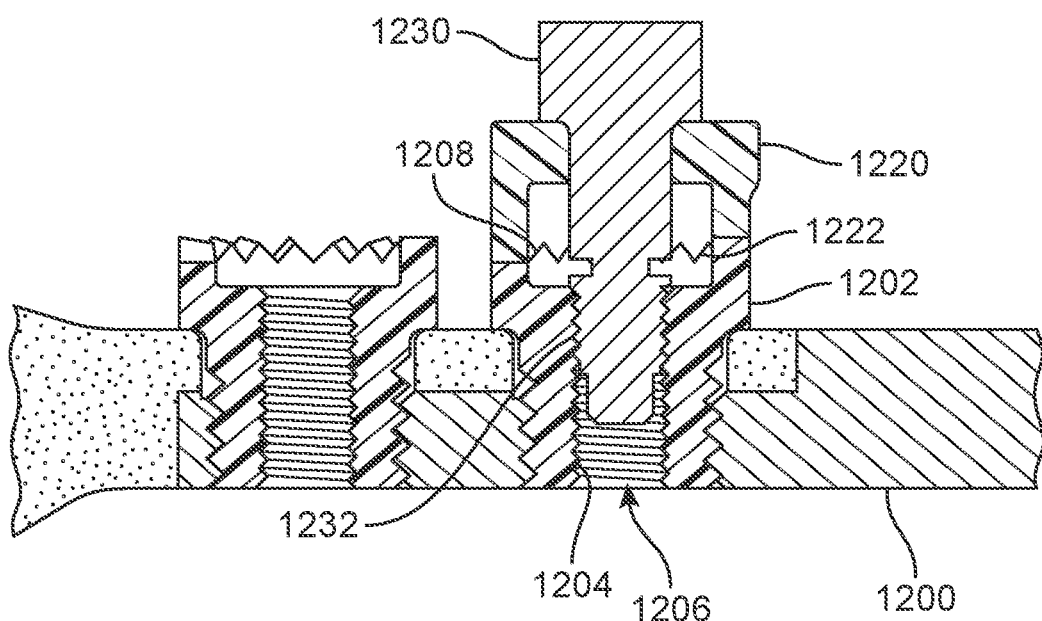

FIGS. 12-14 illustrate views of a connecting portion 1220 of table arm 250 being fastened to a portion of a retractor blade 1200. For purposes of illustration, connecting portion 1220 is shown in isolation. In FIG. 12, connecting portion 1220 is aligned with a connector 1202 of retractor blade 1200, so that fastener 1230 can be inserted through a corresponding hole in connector 1202. Referring next to the cross-sectional views of FIGS. 13 and 14, the threading 1232 of fastener 1230 may engage corresponding threading 1204 that is disposed in the interior cavity 1206 of connector 1202. Rotating fastener 1230 by hand or using a tool drives the end of connecting portion 1220 towards connector 1202. As seen in FIG. 14, when fully fastened, teeth 1222 on connecting portion 1220 may engage teeth 1208 on connector 1202 to prevent any rotation between connecting portion 1220 and connector 1202.

It may be appreciated that this same connection mechanism can be used to connect the ends of any of blade-to-blade articulating arms with connectors on any of the retractor blades. In particular, each of the blade-to-blade articulating arms may be configured with similar connecting portions that can be fastened to connectors on the retractor blades.

Figure 15:
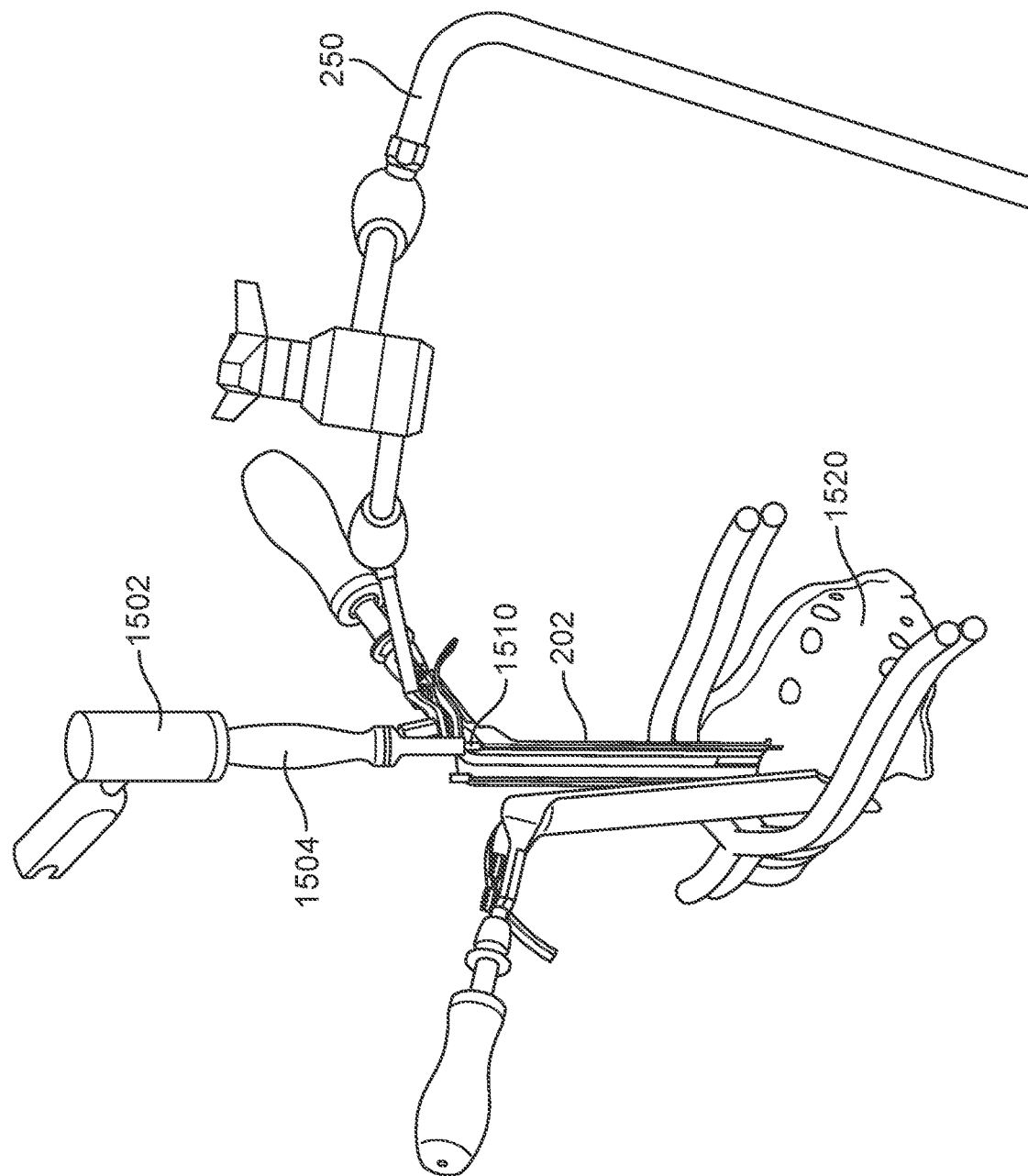
FIGS. 15-16 are schematic views of a retractor blade being temporarily fixed to bony tissue using a fixation pin, according to an embodiment.
Figure 16:
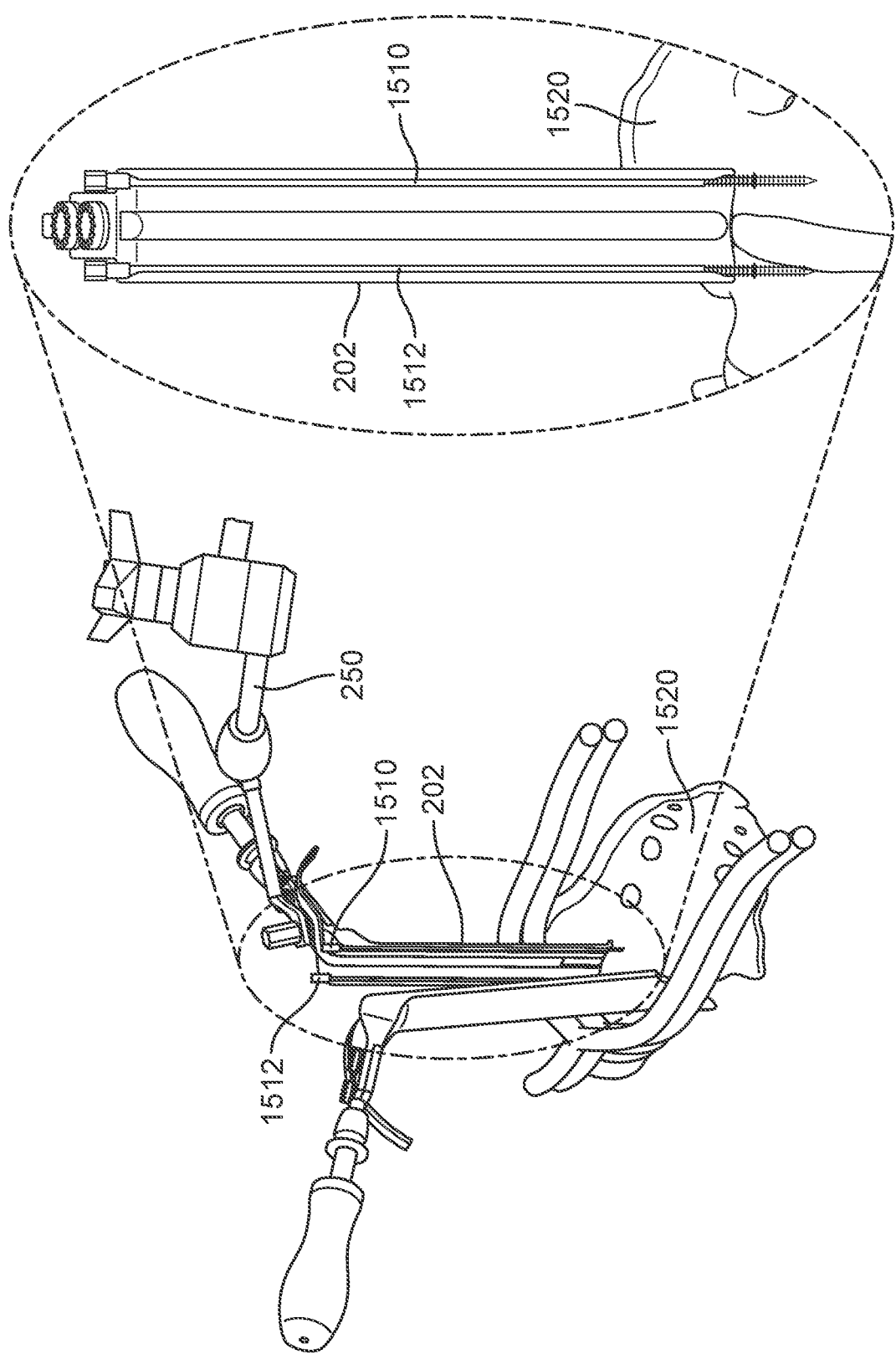

Referring now to FIGS. 15 and 16, with table arm 250 now secured to first retractor blade 202, retractor blade 202 can be further positioned if needed and then secured to the sacrum using a fixation device. In the exemplary embodiment, a fixation pin 1510 is inserted into a corresponding slot of the first retractor blade 202. With the pin inserted, hex driver 1504 can be placed over the head of the pin. A mallet 1502 can be used to initiate insertion of the pin into the bone (FIG. 15). The hex driver 1504 can then be used to fully insert the pin 1510 into sacrum 1520.

FIG. 16 shows retractor blade 202 secured to sacrum 1520 after both fixation pin 1510 and fixation pin 1512 have been inserted into the bone using the above method.

Figure 17:
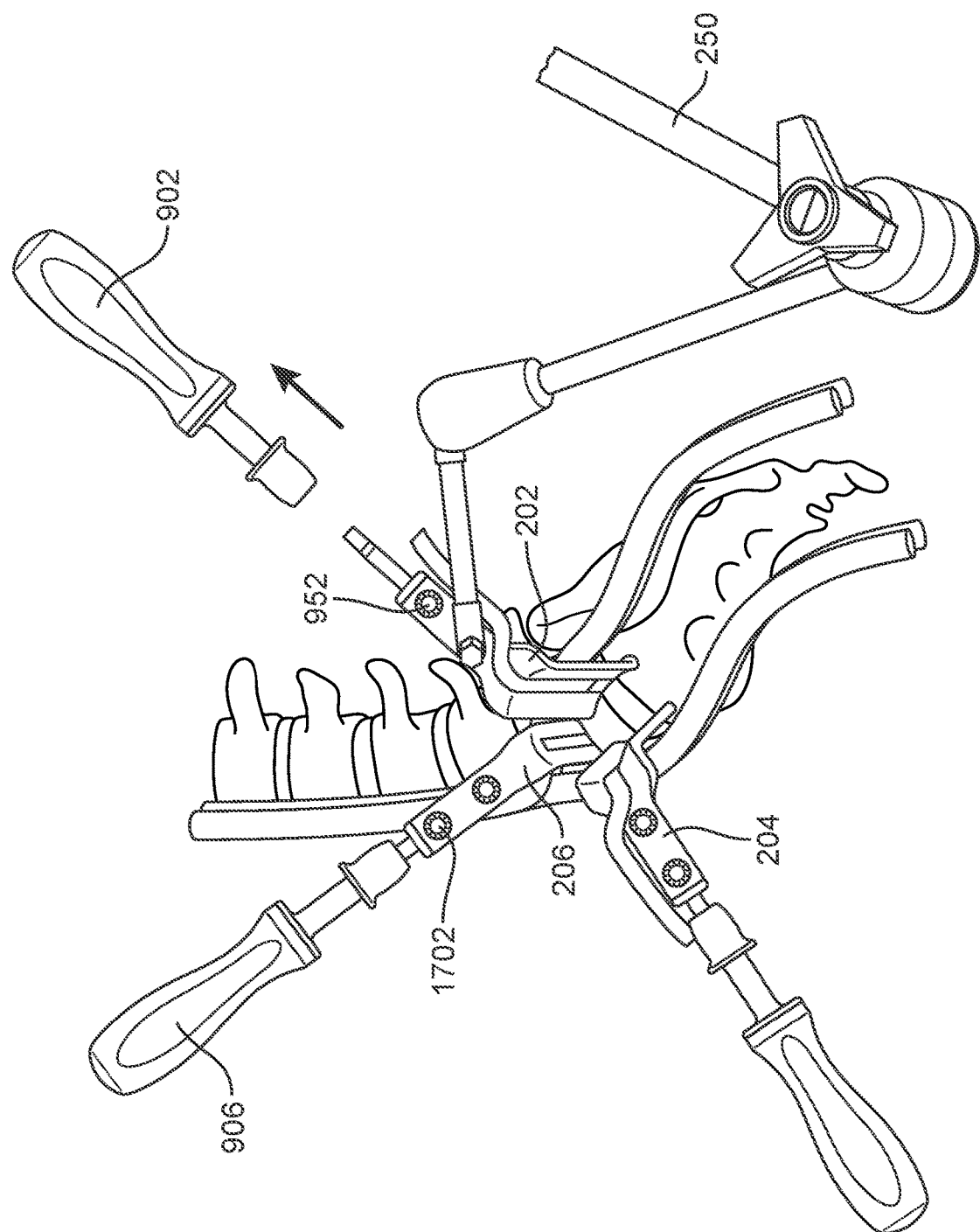
FIGS. 17-21 are schematic views showing three retractor blades being coupled together using two blade-to-blade articulating arms, according to an embodiment.

After first retractor blade 202 has been secured to sacrum 1520 using pins, any additional tightening of the connection between first retractor blade 202 and table arm 250 can be done. Optionally, first releasable handle 902 can be disconnected from retractor blade 202 and removed from the operating area, as shown in FIG. 17, since first retractor blade 202 no longer needs to be manipulated during the procedure.

Third retractor blade 206 (with releasable handle 906 attached) can also be inserted at this time. In this example, third retractor blade 206 is inserted at the bifurcation 1704 of the artery. The surgeon can then manually adjust the position of third retractor blade 206 as needed independently of the positions of both first retractor blade 202 and second retractor blade 204.

Figure 18:
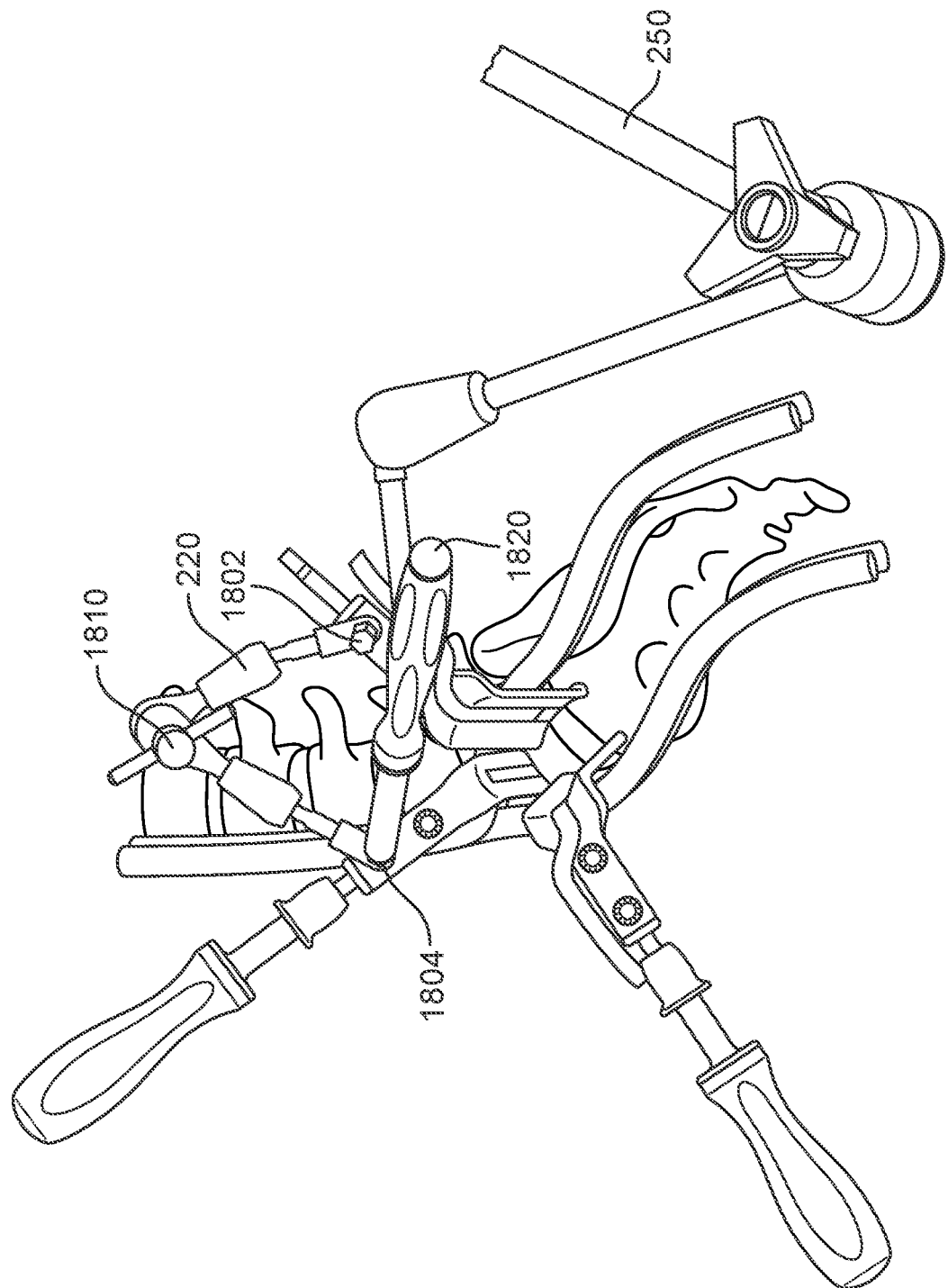

As shown in FIG. 18, third retractor blade 206, once positioned, can be secured to first retractor blade 202 using first blade-to-blade articulating arm 220. Specifically, a first end 1802 of first blade-to-blade articulating arm 220 is fastened to second connector 952 (see FIG. 17) of first retractor blade 202. A second end 1804 of first blade-to-blade articulating arm 220 is then fastened to a connector 1702 (see FIG. 17) of third retractor blade 206. These components may be fastened together in a similar manner to the fastening of table arm 250 to first retractor blade 202, a depicted in FIGS. 12-14. As seen in FIG. 18, a hex driver 1820 may be used to tighten the corresponding fasteners on assembly 220.

Figure 19:
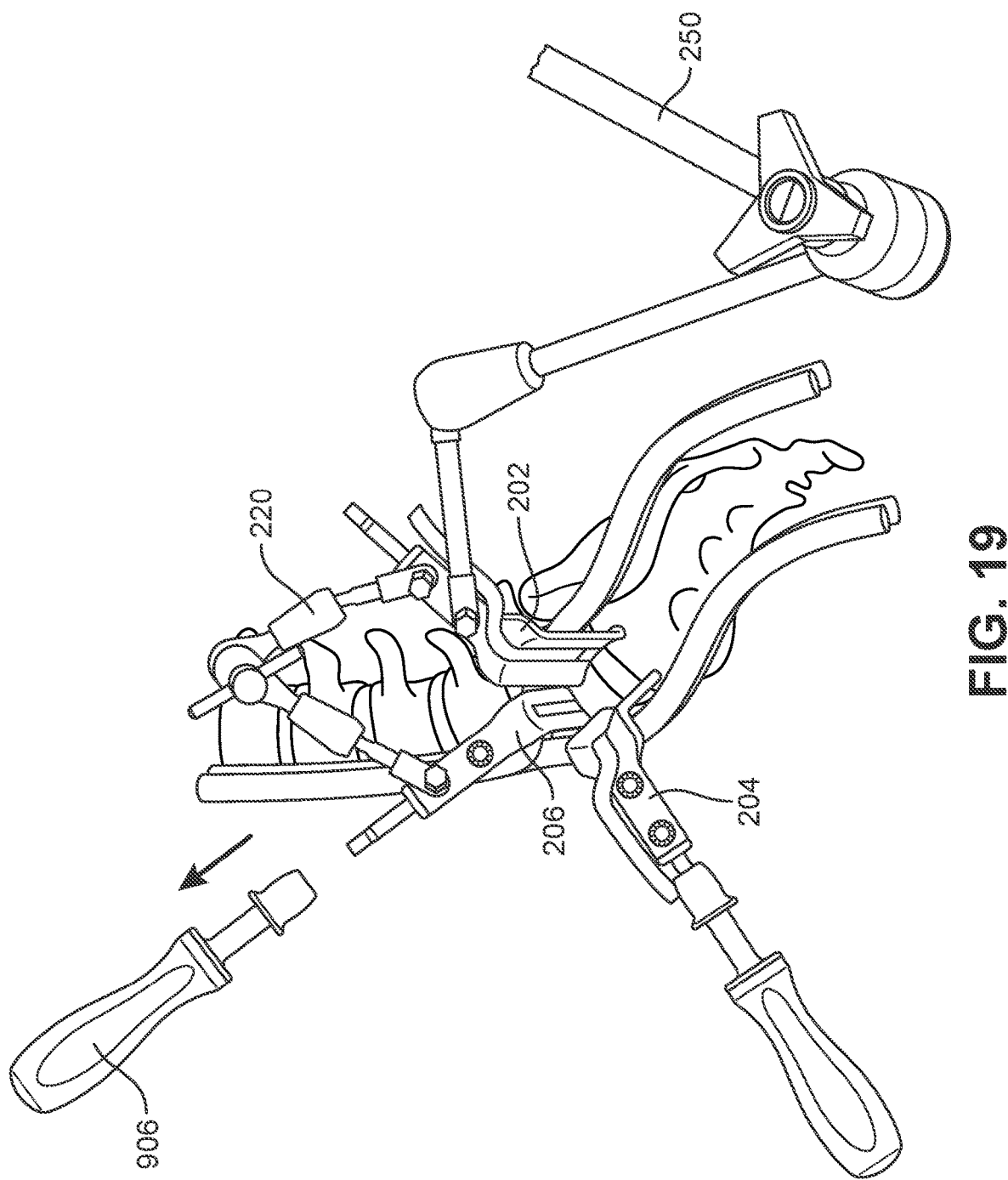

The dynamic range of motion that can be accomplished by blade-to-blade articulating arm 220 by way of the ball-and-socket connections at its ends, and the twisting connection at its center, allows blade-to-blade articulating arm 220 to adapt to any relative configuration of first retractor blade 202 and third retractor blade 206. Moreover, rotating handle 1810 can be used to lock the two main segments of the assembly in place. Once attached to both first retractor blade 202 and third retractor blade 206, first articulating arm 220 may provide a rigid connection between the blades that locks their relative positions in place. At this point, releasable handle 906 can be released from third retractor blade 206, as indicated in FIG. 19.

Figure 20:
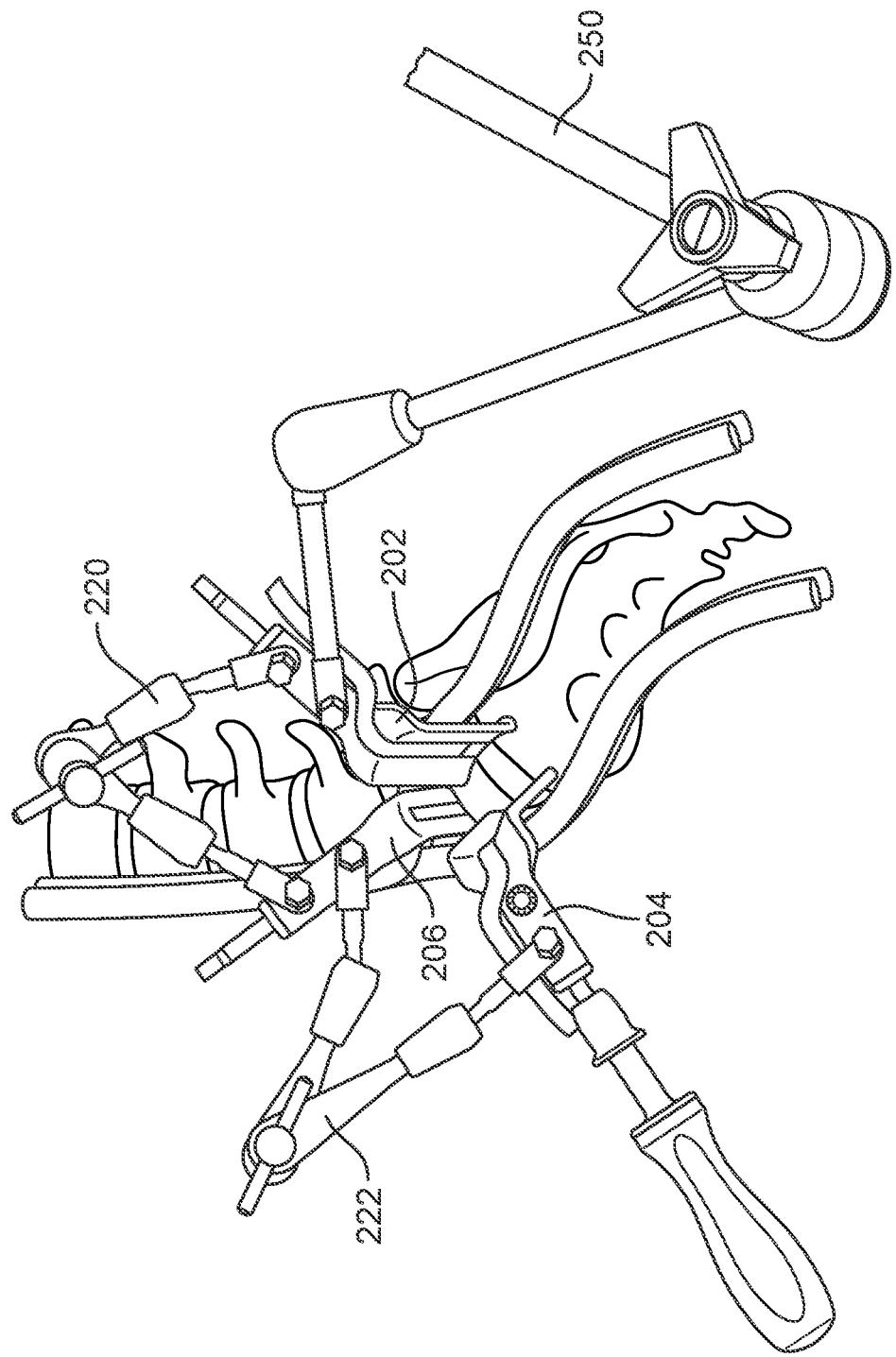
Figure 21:
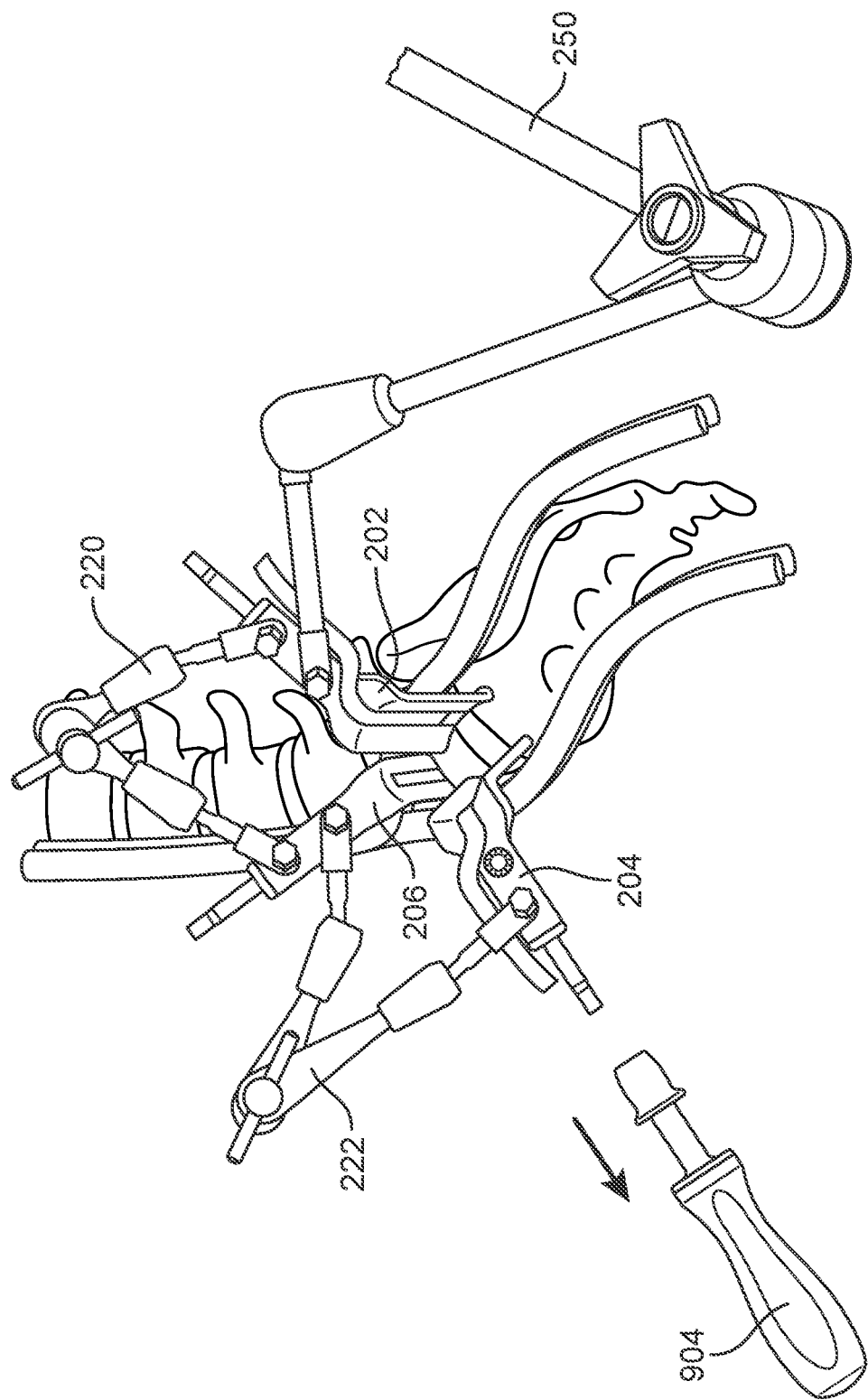

FIG. 20 illustrates the system once second blade-to-blade articulating arm 222 has been used to fix the position of second retractor blade 204. Specifically, second blade-to-blade articulating arm 222 has been secured to third retractor blade 206 at one end, and to second retractor blade 204 at another. Once second blade-to-blade articulating arm 222 has been fastened in place and tightened as needed, second releasable handle 904 can be released from second retractor blade 204, as seen in FIG. 21.

In this final configuration, each retractor blade is fixed in place relative to one another. Specifically, third retractor blade 206 has a fixed position relative to first retractor blade 202 by way of first blade-to-blade articulating arm 220. Likewise, second retractor blade 204 has a fixed position relative to third retractor blade by way of second blade-to-blade articulating arm 222. And second retractor blade 204 and first retractor blade 202 have fixed relative positions by way of their mutual attachments to third retractor blade 206. Additionally, the attachment of first retractor blade 202 to table arm 250 fixes the positions of the blades within the operating area.

Figure 22:
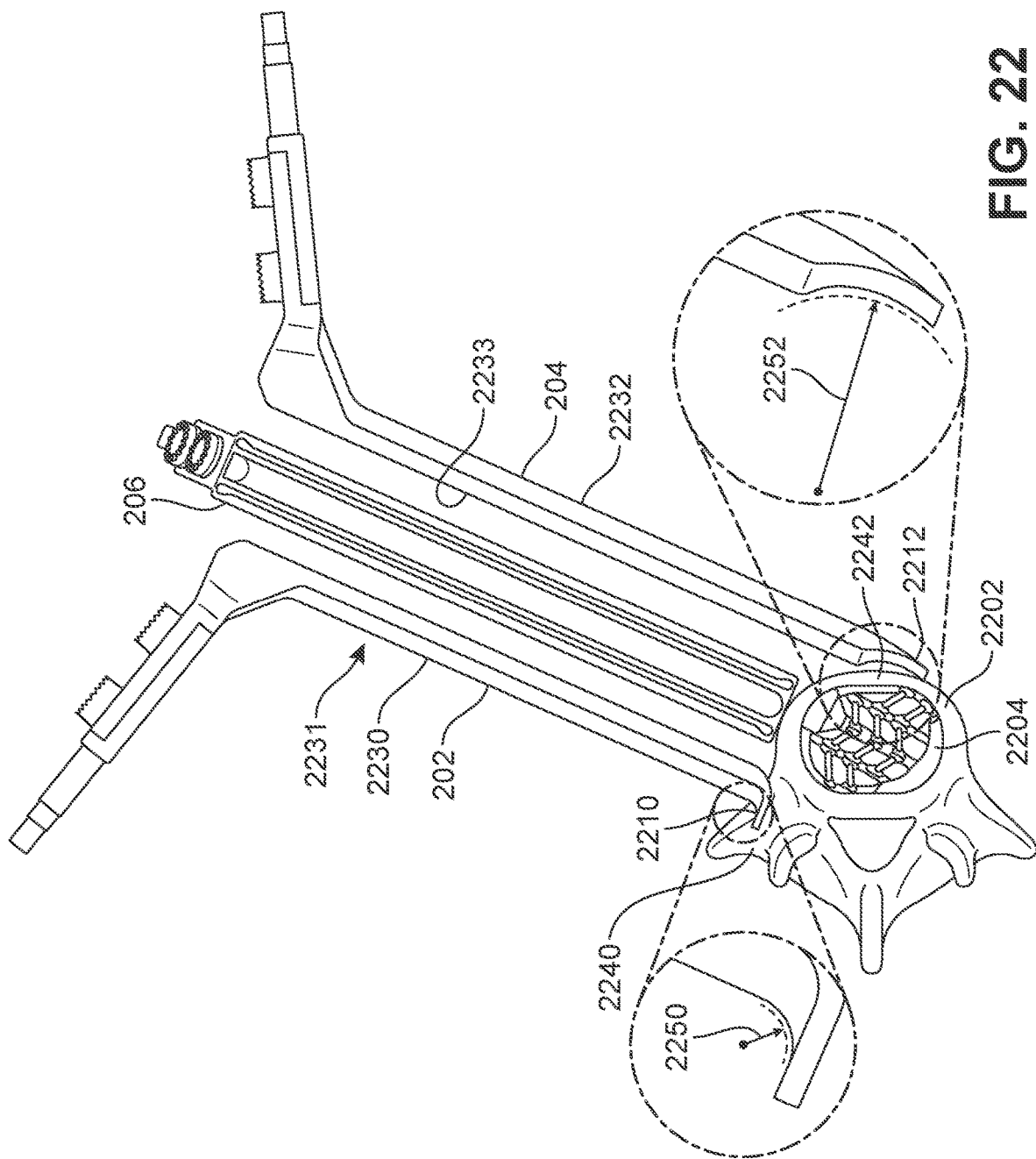
FIG. 22 is a schematic view of three retractor blades aligned with a vertebrae to facilitate insertion of an implant, according to an embodiment.

FIG. 22 depicts a schematic view of the retractor system aligned with a vertebra 2202 along a transverse plane through the body. As seen in FIG. 22, different blades may have different shaped distal ends (or tips) to perform different functions in preparing for an implant. For example, first retractor blade 202 includes a flanged tip 2210 at its distal end that facilitates both retraction of the incision and may help support and stabilize first retractor blade 202 against a posterior portion of vertebra 2202 during and after the fixation of the blade to vertebra 2202 using Steinman pins (as in FIG. 16). In some embodiments, the flanged tip 2210 may be bent at an approximately 90 degree angle away from the rest of first blade portion 2230. Third retractor blade 206 may also have a flanged tip (see, for example, the side view of third blade 206 in FIG. 3) to hold the bifurcation of the artery in place. By contrast, the second retractor blade 204 has a slightly curved (or "cambered") tip 2212 at its distal end. This slight curvature of end 2212 helps the end of second retractor blade 204 to better accommodate the convex surface along an anterior portion 2242 of vertebra 2202.

As illustrated in FIG. 22, the curvature of flanged tip 2210 is substantially greater than the curvature of cambered tip 2212. For clarity, the radius of curvature of each tip is indicated within enlarged views of FIG. 22. Flanged tip 2210 has a first radius of curvature 2250 and cambered tip 2212 has a second radius of curvature 2252, which is substantially larger than first radius of curvature 2250. This increased radius of curvature corresponds with a smaller relative curvature for cambered tip 2212, as curvature is inverse to the radius of curvature.

Not only is the degree of curvature different between flanged tip 2210 and cambered tip 2212, but the direction of curvature is also different. Flanged tip 2210 bends towards a direction that is normal to second side 2231 of first blade portion 2230. In other words, flanged tip 2210 bends behind the first retractor blade as it faces towards a retracted opening in the body. This ensures that flanged tip 2210 can be used to retract and keep tissue away from the retracted opening.

By contrast, cambered tip 2212 bends towards a direction that is normal to first side 2233 of second blade portion 2232. This creates a concave surface for cambered tip 2212 along the first side 2233 of second blade portion 2232. This concave surface is adapted to engage the convex surface of anterior portion 2242 of vertebra 2202.

FIG. 22 also illustrates the difference in length between first retractor blade 202 and second retractor blade 204. Here, first blade portion 2232 of second retractor blade 204 is seen to be slightly longer than a corresponding second blade portion 2230 of first retractor blade 204. The difference in length accommodates the different distances between the incision and different locations along the vertebra. In particular, the distance between the incision and posterior portion 2240 of vertebra 2202 is slightly less than the distance between the incision and anterior portion 2242 of vertebra 2202, due to the orientation of the body during the OLIF procedure. Thus, first retractor blade 202 has a slightly shorter length than the length of second retractor blade 204, to accommodate these different distances and ensure the end of each retractor blade is able to engage the appropriate portion of vertebra 2202. For purposes of illustration, the different lengths for first retractor blade 202 and second retractor blade 204 are indicated in FIG. 3, as first length 290 and second length 292, respectively.

In one embodiment, a ratio between the first length and the second length may be in a range between approximately 90 percent and approximately 97 percent. That is, first blade portion 2230 may be somewhere between 90 percent to 97 percent shorter than second blade portion 2232. In one embodiment, first blade portion 2230 has a length of 140 mm, while second blade portion 2232 has a length of 150 mm. In another embodiment, first blade portion 2230 has a length of approximately 170 mm, while second blade portion 2232 has a length of approximately 180 mm. In another embodiment, first blade portion 2230 has a length of approximately 200 mm, while second blade portion 2232 has a length of approximately 210 mm.

Once retraction is complete, discectomy and endplate preparation will be completed. Next, an implant specifically designed for the OLIF approach (approximately 25° off the coronal plane) will be implanted. When inserted using an approach 25° off the coronal plane, the lordosis of the implant will be correctly aligned with the lordosis of the spine. In FIG. 22, following retraction, an implant 2204 has been successfully inserted between vertebra 2202 and an adjacent vertebra or part of the sacrum.

Figure 23:
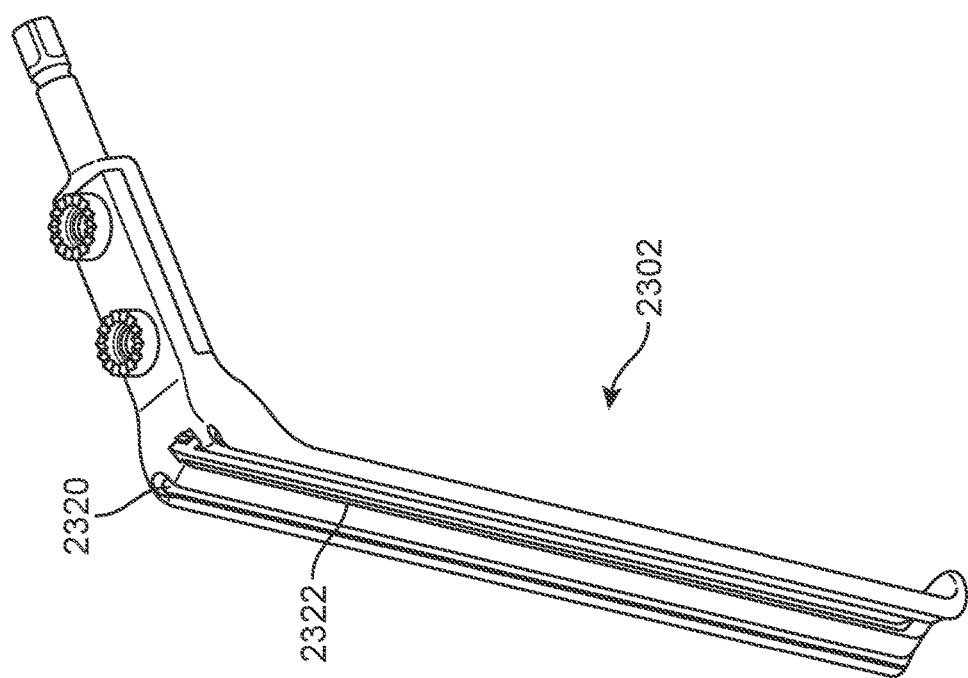

In some embodiments, each of the three blades that comprise the retractor system could have different geometries and/or dimensions. In one embodiment, for example, first retractor blade 202 has the geometry of retractor blade 500 shown in FIG. 5. The geometry of third retractor blade 206 may be similar to that of first retractor blade 202 with some modifications. As an example, in some embodiments, third retractor blade 206 may have the geometry of the blade shown in FIG. 23. The geometry of blade 2302 may be similar in some respects to retractor blade 500. In particular, retractor blade 2302 may include similar channels 2320 for receiving Steinman pins, as well as a central channel 2322 for receiving an illumination device. However, in some cases, retractor blade 2302 may be substantially narrower than retractor blade 500. For example, in one embodiment, first retractor blade 202 could have a width of approximately 30 mm, while third retractor blade 206 could have a width of approximately 20 mm. This narrower width may help third retractor blade 206 to better fit into the bifurcation of an artery.

Figure 24:
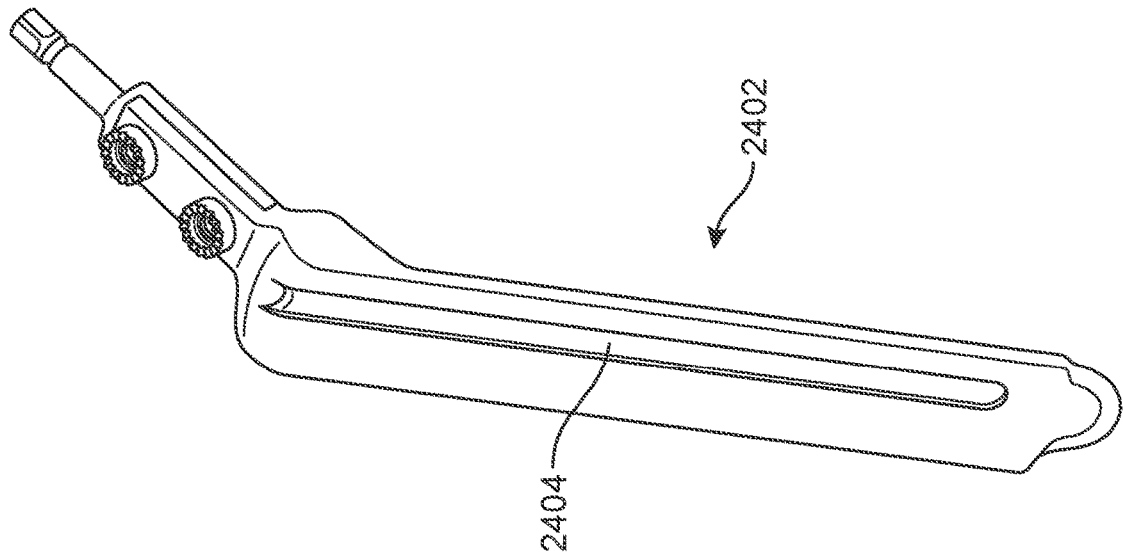
FIGS. 23-27 are schematic views of different retractor blade geometries, according to an embodiment.

In some embodiments, second retractor blade 204 may have a similar geometry to retractor blade 2402 shown in FIG. 24. As seen in comparing FIGS. 23 and 24, retractor blade 2402 has a slightly different geometry to retractor blade 2302. Specifically, retractor blade 2402 lacks channels for receiving pins, though it does include a central channel 2404. Additionally, the rounded tip 2406 may help engaging tissue for mobilization.

Figure 27:
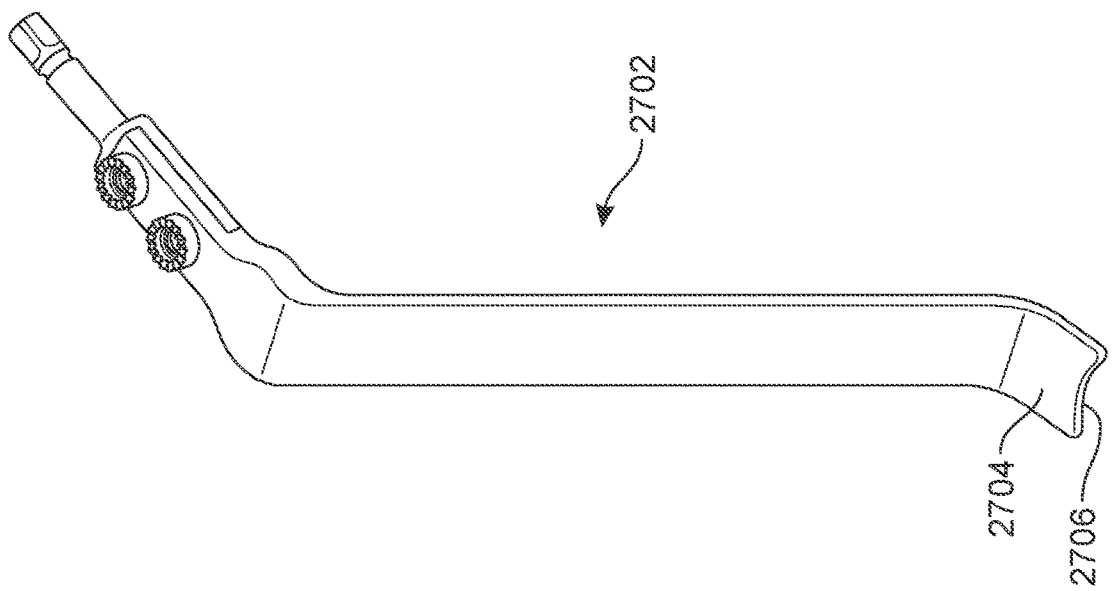
Figure 26:
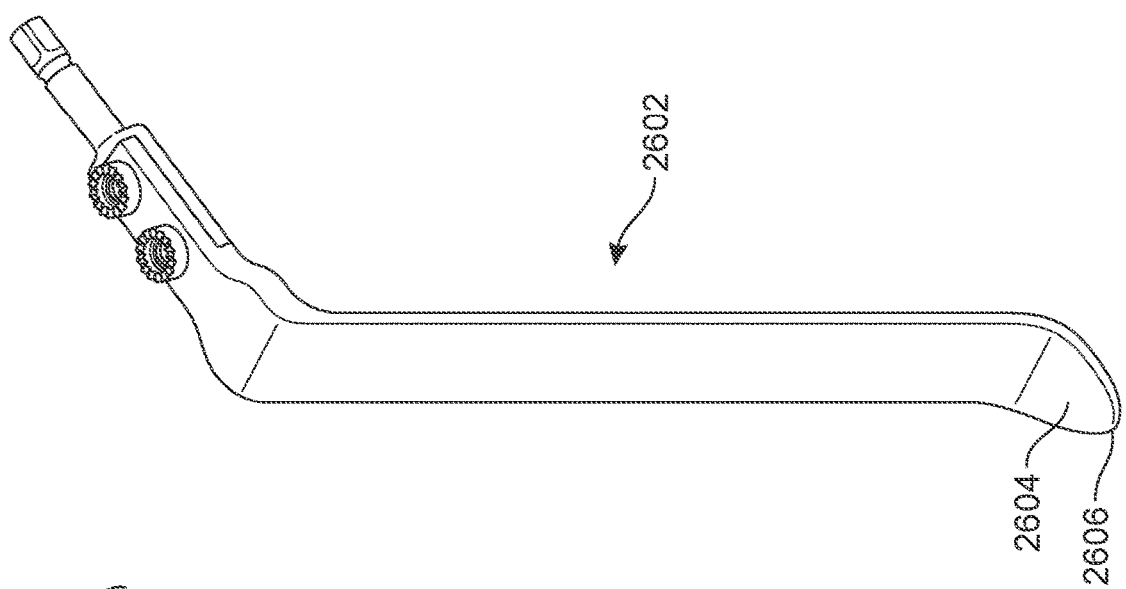
Figure 25:
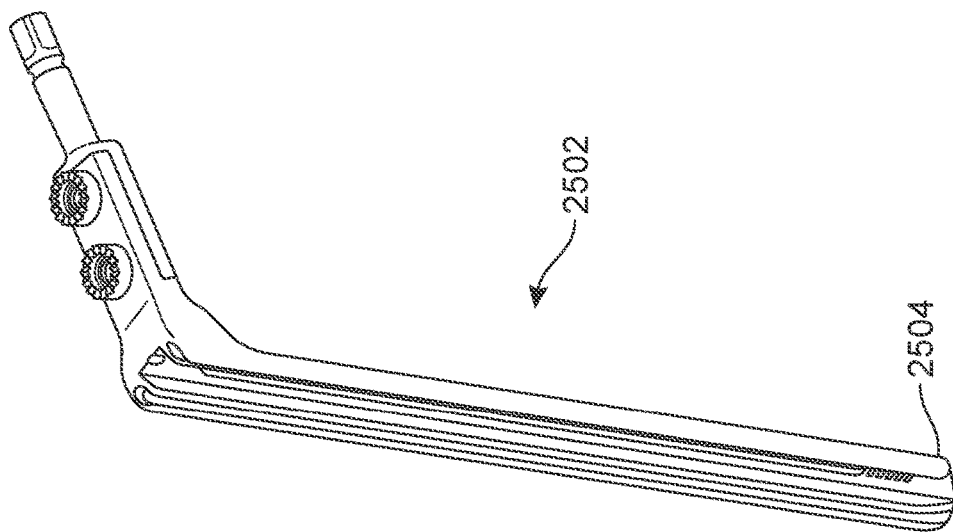

Still other variations in blade design are possible. For example, FIGS. 25 through 27 illustrate schematic views of variations in the geometry of the blade ends. For example, some embodiments could include a blade 2502 with a substantially straight end 2504, as depicted in FIG. 25. Some embodiments could include a blade 2602 with a bent end 2604 having a convex tip 2606, as depicted in FIG. 26. Other embodiments could include a blade 2702 with a bent end 2704 having a concave tip 2706, as depicted in FIG. 27. The type of blade tip geometry may be selected according to the type of tissue that must be retracted.

As already discussed, the modular retraction system of the embodiments is configured to build a rigid frame outside of the body after the blades have been properly positioned by hand and pinned to a vertebral body.

The present system gives the surgeon the flexibility to place the blades wherever they want without being limited by a rigid frame. This ensures that the blades are placed perfectly every time based on unique anatomic structures while still providing a rigid frame once the components of the system have been assembled and tightened. Placing the retractor blades by hand provides the surgeon with tactile feedback to help reduce the risk of vascular injury. Blade to blade fixation eliminates the need for someone (typically a physician assistant) to hold one of the blades in place during the procedure. If two blade to blade connections are used, this eliminates the need for a second table arm and removes clutter from the sterile field.

While the exemplary embodiments describe using the modular retractor system to prepare for an OLIF approach at L5-S1 between the bifurcation, it can also be utilized for an OLIF approach at levels higher up in the lumbar spine. Furthermore, the retractor blades could be utilized for any surgical approach, spine or otherwise, that requires soft tissue retraction.

It is contemplated that in some embodiments interchangeable parts of a modular retractor system could be prepared as kits that can be accessed prior to, or during, a surgical procedure. The kits could be prepared to include multiple retractor blades, releasable handles, blade-to-blade articulating arms, table arms, fixation pins, fastening tools such as hex drivers, and illumination devices.

For each of the three retractor blades described above (e.g., first retractor blade 202, second retractor blade 204, and third retractor blade 206) a kit could be configured with interchangeable blades having different dimensions (for example, different lengths). As an example, a kit could include three different sizes associated with first retractor blade 202. These could include a 140 mm length blade, a 170 mm length blade, and a 200 mm length blade. Additionally, a kit could include three different sizes of retractor blades associated with second retractor blade 204. These could include a 150 mm length blade, a 180 mm length blade, and a 210 mm length blade. Furthermore, a kit could include three different sizes of retractor blades associated with third retractor blade 206. These could include a 140 mm length blade, a 170 mm length blade, and a 200 mm length blade.

While various embodiments have been described, the description is intended to be exemplary, rather than limiting and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A retractor system, comprising:
a first blade assembly comprising a first retractor blade;
a second blade assembly comprising a second retractor blade;
a table arm, the table arm including a first end and a second end, wherein the first end is configured to be secured in place adjacent an operating area;
a blade-to-blade articulating arm including a first end and a second end;
wherein the second end of the table arm can be fastened to the first retractor blade;
wherein the first end of the blade-to-blade articulating arm can be fastened to the first retractor blade; and
wherein the second end of the blade-to-blade articulating arm can be fastened to the second retractor blade;
wherein the blade-to-blade articulating arm consists essentially of:
a first blade connector at a first end;
a second blade connector at a second end; and
an articulating flex arm including a central articulating joint and being connectable to the first blade connector with a first ball and socket joint and connectable to the second blade connector with a second ball and socket joint.

2. The retractor system according to claim 1, wherein:
the first retractor blade includes a first connector and a second connector;
wherein the second end of the table arm can be fastened to the first connector;
wherein the first end of the blade-to-blade articulating arm can be fastened to the second connector.

3. The retractor system according to claim 1, wherein the first retractor blade includes a slot for receiving a fixation device.

4. The retractor system according to claim 1, wherein the fixation device is a Steinman pin.

5. The retractor system according to claim 1, wherein the first retractor blade includes a central channel for receiving an illumination device.

6. The retractor system according to claim 1, wherein the first blade assembly includes a releasable handle member configured to be releasably connected to a connecting end of the first retractor blade.

7. The retractor system according to claim 1, wherein the blade-to-blade articulating arm includes a first segment and a second segment that rotate about a common axis.

8. A retractor system, comprising:
a first retractor blade, a second retractor blade, and a third retractor blade;
a table arm, the table arm including a first end and a second end, wherein the first end is configured to be secured in place adjacent an operating area;
a first blade-to-blade articulating arm including a first end and a second end;
a second blade-to-blade articulating arm including a first end and a second end;
wherein each of the first retractor blade, the second retractor blade and the third retractor blade comprises two connectors;
wherein, on each of the first retractor blade, the second retractor blade, and the third retractor blade, the two connectors on a given retractor blade are of the same type;
wherein an end of the table arm is configured to fasten to a first connector of the first retractor blade;
wherein a first end of the first blade-to-blade articulating arm is configured to fasten to a second connector of the first retractor blade;
wherein a second end of the first blade-to-blade articulating arm is configured to fasten to a first connector of the second retractor blade;
wherein a first end of the second blade-to-blade articulating arm is configured to fasten to a second connector of the second retractor blade; and
wherein a second end of the second blade-to-blade articulating arm is configured to fasten to a connector of the third retractor blade.

9. The retractor system according to claim 8, wherein each of the first retractor blade, the second retractor blade, and the third retractor blade include an end that can be coupled to a releasable handle.

10. The retractor system according to claim 8, wherein each of the first blade-to-blade articulating arm and the second blade-to-blade articulating arm includes a first segment and a second segment that rotate about a common axis.

11. The retractor system according to claim 8, wherein each of the first blade-to-blade articulating arm and the second blade-to-blade articulating arm includes a first ball-and-socket connection adjacent the first end and a second ball-and-socket connection adjacent the second end.

12. The retractor system according to claim 8, wherein the first retractor blade includes a slot for receiving a Steinman pin.

13. The retractor system according to claim 8, wherein the first retractor blade includes a channel for receiving an illumination device.

14. A method of positioning a retractor system within a body, the method comprising the steps of:
 inserting a first retractor blade into an incision in the body;
 inserting a second retractor blade into the incision after the first retractor blade has been inserted, wherein the second retractor blade can be positioned independently of the first retractor blade;
 coupling an end of a table arm to a first connector of the first retractor blade;
 inserting a third retractor blade into the incision after the first retractor blade and the second retractor blade have been inserted;
 wherein each of the first retractor blade, the second retractor blade and the third retractor blade comprises a first connector and a second connector; and
 wherein, on each of the first retractor blade, the second retractor blade, and the third retractor blade, the two connectors on a given retractor blade are of the same type;
 coupling a first end of a first blade-to-blade articulating arm to the second connector of the first retractor blade and coupling a second end of the first blade-to-blade articulating arm to the first connector of the second retractor blade; and
 coupling a first end of a second blade-to-blade articulating arm to the second connector of the second retractor blade and coupling a second end of the second blade-to-blade articulating arm to the first connector of the third retractor blade.

15. The method according to claim 14, wherein the table arm is attached to an operating table.

16. The method according to claim 15, wherein inserting the first retractor blade includes using a releasable handle coupled to the first retractor blade to insert and position the first retractor blade within in the body.

17. The method according to claim 16, wherein the method includes a step of disconnecting the releasable handle from the first retractor blade prior to coupling the first end of the blade-to-blade articulating arm to the first retractor blade.

18. The method according to claim 14, wherein coupling the first end of the first blade-to-blade articulating arm to the first retractor blade includes using a fastening tool.

19. The method according to claim 14, wherein the method further includes a step of temporarily fixing the first retractor blade to bony tissue by inserting a pin through a slot in the first retractor blade.

* * * * *